US010251949B2

(12) United States Patent
Grønvold et al.

(10) Patent No.: US 10,251,949 B2
(45) Date of Patent: *Apr. 9, 2019

(54) STABILIZED HIV-1 PEPTIDE CONSTRUCTS COMPRISING THE GP120 C5 DOMAIN AND GP41 HYDROPHILIC DOMAIN

(71) Applicant: Bionor Immuno AS, Skien (NO)

(72) Inventors: Maja Sommerfelt Grønvold, Risør (NO); Angus Dalgleish, Cheaham (GB); Einar Tønnes Lange, Skien (NO); Jens Olof Holmberg, Helsingborg (SE); Per Bengtsson, Malmö (SE); Birger Sørensen, Skien (NO)

(73) Assignee: BIONOR IMMUNO AS, Skien (NO)

( * ) Notice: Subject to any disclaimer, the term of this patent is extended or adjusted under 35 U.S.C. 154(b) by 45 days.

This patent is subject to a terminal disclaimer.

(21) Appl. No.: 14/952,292

(22) Filed: Nov. 25, 2015

(65) Prior Publication Data

US 2016/0144019 A1 May 26, 2016

Related U.S. Application Data

(63) Continuation of application No. 13/382,137, filed as application No. PCT/EP2010/059513 on Jul. 3, 2010, now Pat. No. 9,200,065.

(60) Provisional application No. 61/223,436, filed on Jul. 7, 2009.

(30) Foreign Application Priority Data

Jul. 3, 2009 (EP) .................................... 09164565

(51) Int. Cl.
    A61K 39/21    (2006.01)
    C07K 14/005   (2006.01)
    C07K 16/10    (2006.01)
    A61K 39/12    (2006.01)
    C12N 7/00     (2006.01)
    A61K 39/00    (2006.01)

(52) U.S. Cl.
    CPC .............. A61K 39/21 (2013.01); A61K 39/12 (2013.01); C07K 14/005 (2013.01); C07K 16/1063 (2013.01); C12N 7/00 (2013.01); A61K 2039/505 (2013.01); A61K 2039/5258 (2013.01); A61K 2039/53 (2013.01); A61K 2039/545 (2013.01); A61K 2039/627 (2013.01); C12N 2740/16122 (2013.01); C12N 2740/16134 (2013.01); C12N 2740/16171 (2013.01)

(58) Field of Classification Search
    CPC ...... A61K 39/12; A61K 39/21; C07K 14/005; C12N 2740/16134; C12N 2740/16122
    See application file for complete search history.

(56) References Cited

U.S. PATENT DOCUMENTS 6,911,527 B1  6/2005 Scala et al.
2012/0263720 A1  10/2012 Grønvold et al.

FOREIGN PATENT DOCUMENTS

CN        1195702 A       10/1998
WO    WO 92/05196 A1      4/1992
WO   WO 2009/042895 A2    4/2009
WO   WO 2009/099777 A2    8/2009

OTHER PUBLICATIONS

Gray, E. S., et al., 2008, 4E10-resistant variants in a human immunodeficiency virus type 1 subtype C-infected individual with an anti-membrane-proximal external region-neutralizing antibody response, J. Virol. 82(5):2367-2375.*
Ingale, S., et al., 2010, Synthesis and analysis of the membrane proximal external region epitopes of HIV-1, J. Pept. Sci. 16:716-722.*
Kim, M., et al., 2013, Immunogenicity of membrane-bound HIV-1 gp41 membrane-proximal external region (MPER) segments is dominated by residue accessibility and modulated by stereochemistry, J. Biol. Chem. 288(44):31888-31901.*
Brown, L. et al., "The conserved carboxy terminal region of HIV-1 gp120 is recognized by seronegative HIV-exposed people," *AIDS* 13(18):2515-2521, Lippincott Williams & Wilkins, United States (1999).
Cadogan, M. et al., "HLA Homology within the C5 Domain Promotes Peptide Binding by HIV Type 1 gp120," *AIDS Research and Human Retroviruses* 24(6):845-855, Mary Ann Liebert Inc., United States (2008).
Easterbrook, P.J. et al., "Chemokine Receptor Polymorphisms and Human Immunodeficiency Virus Disease Progression," *JID* 180:1096-1105, Infectious Diseases Society of America, United States (1999).
Gougeon, M-L. et al., "Programmed Cell Death in Peripheral Lymphocytes from HIV-Infected Persons: Increased Susceptibility to Apoptosis of CD4 and CD8 T Cells Correlates with Lymphocyte Activation and with Disease Progression," *Journal of Immunology* 156:3509-3520, American Association of Immunologists, United States (1996).
Guilhaudis, L. et al., "Solution structure of the HIV gp120 C5 Domain ," *Eur. J. Biochem.* 269:4860-4867, FEBS, England (2002).
Letvin, N.L. et al., "Progress and obstacles in the development of an AIDS vaccine," *Nature Reviews* 6:930-939, Nature Publishing Group, England (2006).
Liegler, T.J. et al., "Diminished Spontaneous Apoptosis in Lymphocytes from Human Immunodeficiency Virus-Infected Long-Term Nonprogressors," *J. Infect. Dis.* 178:669-679, Infectious Diseases Society of America, United States (1998).

(Continued)

Primary Examiner — Jeffrey S Parkin
(74) Attorney, Agent, or Firm — Womble Bond Dickinson (US) LLP

(57) ABSTRACT

Disclosed is a method for treatment of HIV related diseases comprising targeting complexes between on the one hand the C5 domain of gp120 and on the other hand gp41 or the C2 domain of gp120. The complexes may be stabilised by administering compounds, such as antibodies, capable of directly interacting with and stabilising the complex, or by immunizing with C5 and gp41/C2 derived material so as to induce antibodies that bind to and stabilise the complex.

11 Claims, 3 Drawing Sheets

Figure 1:
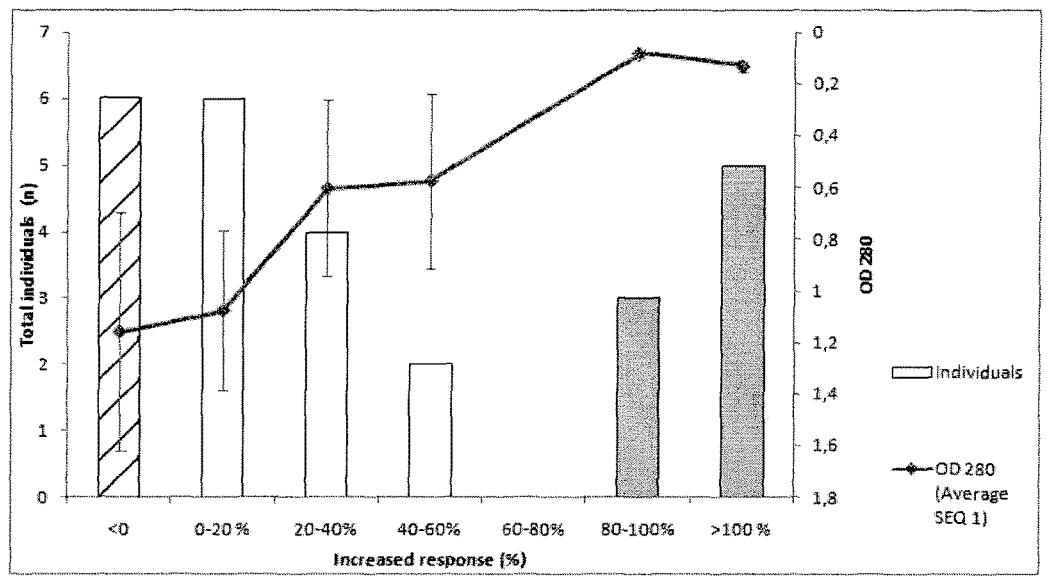

Specification includes a Sequence Listing.

(56) References Cited

OTHER PUBLICATIONS

Lifson, A.R. et al., "Long-Term Human Immunodeficiency Virus Infection in Asymptomatic Homosexual and Bisexual Men with Normal CD4+ Lymphocyte Counts: Immunologic and Virologic Characteristics," *J. Infect. Dis. 163*:959-965, The University of Chicago, United States (1991).
Loomis-Price, L.D. et al., "Correlation between Humoral Responses to Human Immunodeficiency Virus Type 1 Envelope and Disease Progression in Early-Stage Infection," *J. Infect. Dis. 178*:1306-1316, Infectious Diseases Society of America, United States (1998).
Luo, M. et al., "Induction of neutralizing antibody against human immunodeficiency virus type 1 (HIV-1) by immunization with gp41 membrane-proximal external region (MPER) fused with porcine endogenous retrovirus (PERV) p15E fragment," *Vaccine 24*:435-442, Elsevier Ltd., England (2006).
Mascola, J.R. et al., "Protection of Macaques against Pathogenic Simian/Human Immunodeficiency Virus 89.6PD by Passive Transfer of Neutralizing Antibodies," *Journal of Virology 73(5)*:4009-4018, American Society for Microbiology, United States (1999).
Mascola, J.R. et al., "Protection of macaques against vaginal transmission of a pathogenic HIV-1/SIV chimeric virus by passive infusion of neutralizing antibodies," *Nature Medicine 6(2)*:207-210, Nature America Inc., United States (2000).
Montero, M. et al., "The Membrane-Proximal External Region of the Human Immunodeficiency Virus Type 1 Envelope: Dominant Site of Antibody Neutralization and Target for Vaccine Design," *Microbiology and Molecular Reviews 72(1)*:54-84, American Society for Microbiology, United States (2008).
Muro-Cacho, C-A. et al., "Analysis of Apoptosis in Lymph Nodes of HIV-Infected Persons: Intensity of Apoptosis Correlates with the General State of Activation of the Lymphoid Tissue and Not with Stage of Disease or Viral Burden," *Journal of Immunology 154*:5555-5566, American Association of Immunologists, United States (1995).
Song, L. et al., "Broadly neutralizing anti-HIV-1 antibodies disrupt a hinge-related function of gp41 at the membrane interface," *PNAS 106(22)*:9057-9062, National Academy of Science, United States (2009).
Sreepain, A. et al., "Conserved Neutralizing Epitopes of HIV Type 1 CRF01_AE against Primary Isolates in Long-Term Nonprogressors," *AIDS Research and Human Retroviruses 20(5)*:531-542, Mary Ann Liebert, Inc., England (2004).
Sun, Z-Y.J. et al., "HIV-1 Broadly Neutralizing Antibody Extracts Its Epitope from a Kinked gp41 Ectodomain Region on the Viral Membrane," *Immunity 28*:52-63, Elseveir Inc., United States (2008).
Warren, R.Q. et al., "Patterns of Antibody Reactivity to Selected Human Immunodeficiency Virus Type 1 (HIV-1) gp160 Epitopes in Infected Individuals Grouped According to CD4+ Cell Levels," *Journal of Clinical Immunology 11(1)*:13-21, Plenum Publishing Corporation, United States (1991).
Wong, M.T. et al., "Longitudinal Analysis of the Humoral Immune Response to Human Immunodeficiency Virus Type 1 (HIV-1) gp160 Epitopes in Rapidly Progressing and Nonprogressing HIV-1-Infected Subjects," *J. Infect. Dis. 168*:1523-1527, University of Chicago Press, United States(1993).
Zhang, M-Y. and Dimitrov, D.S., "Novel Approaches for Identification of Broadly Cross-Reactive HIV-1 Neutralizing Human Monoclonal Antibodies and Improvement of Their Potency," *Current Pharmaceutical Design 13*:203-212, Bentham Science Publishers, Netherlands (2007).
International Search Report and Written Opinion for International Patent Application No. PCT/EP2010/059513, European Patent Office, Netherlands, dated Jan. 27, 2011.
International Preliminary Report on Patentability for International Patent Application No. PCT/EP2010/059513, European Patent Office, Germany, dated Dec. 21, 2011.
Labrosse, B., et al., "Sensitivity to a Nonpeptidic Compound (RPR103611) Blocking Human Immunodeficiency Virus Type 1 Env-Mediated Fusion Depends on Sequence and Accessibility of the gp41 Loop Region," *Journal of Virology 74*:2142-2150, American Society for Microbiology, United States (2000).
Wyatt, R., et al., "Analysis of the Interaction of the Human Immunodeficiency Virus Type 1 gp120 Envelope Glycoprotein with the gp41 Transmembrane Glycoprotein," *Journal of Virology 71*:9722-9731, American Society for Microbiology, United States (1997).
Gray, E.S., et al., "4E10-Resistant Variants in a Human Immunodeficiency Virus Type 1 Subtype C-Infected Individual with an Anti-Membrane-Proximal External Region-Neutralizing Antibody Response," *Journal of Virology 82(5)*:2367-2375, American Society for Microbiology, United States (2008).
Kim, M., et al., "Immunogenicity of Membrane-bound HIV-1 gp41 Membrane-proximal External Region (MPER) Segments Is Dominated by Residue Accessibility and Modulated by Stereochemistry," *Journal of Biological Chemistry 288(44)*:31888-31901, American Society for Biochemistry and Molecular Biology, United States (2013).
Ingale, S., et al., "Synthesis and analysis of the membrane proximal external region epitopes of HIV-1," *Journal of Peptide Science 16*:716-722, John Wiley & Sons, Ltd., United States (2010).
"Hemorrhagic Fever with Renal Syndrome," editor: Yang Weisong, People's Army Medical Press, 1992, pp. 256-264.

\* cited by examiner

SEQUENCE LISTING

<160> NUMBER OF SEQ ID NOS: 61

<210> SEQ ID NO 1
<211> LENGTH: 17
<212> TYPE: PRT
<213> ORGANISM: HIV

<400> SEQUENCE: 1

Ala Pro Thr Lys Ala Lys Arg Arg Val Val Gln Arg Glu Lys Arg Ala
1               5                   10                  15

Val

<210> SEQ ID NO 2
<211> LENGTH: 17
<212> TYPE: PRT
<213> ORGANISM: HIV

<400> SEQUENCE: 2

Ala Pro Thr Lys Ala Lys Arg Arg Val Val Glu Arg Glu Lys Arg Ala
1               5                   10                  15

Val

<210> SEQ ID NO 3
<211> LENGTH: 17
<212> TYPE: PRT
<213> ORGANISM: HIV

<400> SEQUENCE: 3

Ala Pro Thr Arg Ala Lys Arg Arg Val Val Gln Arg Glu Lys Arg Ala
1               5                   10                  15

Val

<210> SEQ ID NO 4
<211> LENGTH: 17
<212> TYPE: PRT
<213> ORGANISM: HIV

<400> SEQUENCE: 4

Ala Pro Thr Arg Ala Lys Arg Arg Val Val Glu Arg Glu Lys Arg Ala
1               5                   10                  15

Val

<210> SEQ ID NO 5
<211> LENGTH: 17
<212> TYPE: PRT
<213> ORGANISM: HIV

<400> SEQUENCE: 5

Ala Pro Thr Glu Ala Lys Arg Arg Val Val Glu Arg Glu Lys Arg Ala
1               5                   10                  15

Val

<210> SEQ ID NO 6
<211> LENGTH: 15
<212> TYPE: PRT
<213> ORGANISM: HIV
<220> FEATURE:
<221> NAME/KEY: MISC_FEATURE
<222> LOCATION: (4)..(4)
<223> OTHER INFORMATION: Glu can be Gly
<220> FEATURE:
<221> NAME/KEY: MISC_FEATURE
<222> LOCATION: (5)..(5)

```
<223> OTHER INFORMATION: Gly can be Arg
<220> FEATURE:
<221> NAME/KEY: MISC_FEATURE
<222> LOCATION: (13)..(13)
<223> OTHER INFORMATION: Arg can be Gln
<220> FEATURE:
<221> NAME/KEY: MISC_FEATURE
<222> LOCATION: (14)..(14)
<223> OTHER INFORMATION: Asp can be Gly
<220> FEATURE:
<221> NAME/KEY: MISC_FEATURE
<222> LOCATION: (15)..(15)
<223> OTHER INFORMATION: Arg can be Lys

<400> SEQUENCE: 6

Asp Arg Pro Glu Gly Ile Glu Glu Glu Gly Gly Glu Arg Asp Arg
1               5                   10                  15

<210> SEQ ID NO 7
<211> LENGTH: 15
<212> TYPE: PRT
<213> ORGANISM: HIV
<220> FEATURE:
<221> NAME/KEY: MISC_FEATURE
<222> LOCATION: (4)..(4)
<223> OTHER INFORMATION: Glu can be Gly
<220> FEATURE:
<221> NAME/KEY: MISC_FEATURE
<222> LOCATION: (5)..(5)
<223> OTHER INFORMATION: Gly can be Arg
<220> FEATURE:
<221> NAME/KEY: MISC_FEATURE
<222> LOCATION: (13)..(13)
<223> OTHER INFORMATION: Arg can be Gln
<220> FEATURE:
<221> NAME/KEY: MISC_FEATURE
<222> LOCATION: (14)..(14)
<223> OTHER INFORMATION: Asp can be Gly
<220> FEATURE:
<221> NAME/KEY: MISC_FEATURE
<222> LOCATION: (15)..(15)
<223> OTHER INFORMATION: Arg can be Lys

<400> SEQUENCE: 7

Asp Arg Pro Glu Gly Ile Glu Asn Asn Gly Gly Glu Arg Asp Arg
1               5                   10                  15

<210> SEQ ID NO 8
<211> LENGTH: 12
<212> TYPE: PRT
<213> ORGANISM: HIV

<400> SEQUENCE: 8

Val Glu Arg Tyr Leu Lys Asp Gln Gln Leu Leu Gly
1               5                   10

<210> SEQ ID NO 9
<211> LENGTH: 12
<212> TYPE: PRT
<213> ORGANISM: HIV

<400> SEQUENCE: 9

Val Glu Arg Tyr Leu Lys Asp Glu Glu Leu Leu Gly
1               5                   10

<210> SEQ ID NO 10
<211> LENGTH: 12
<212> TYPE: PRT
<213> ORGANISM: HIV

<400> SEQUENCE: 10
```

Val Glu Arg Tyr Leu Lys Asp Asn Asn Leu Leu Gly
1               5                   10

<210> SEQ ID NO 11
<211> LENGTH: 15
<212> TYPE: PRT
<213> ORGANISM: HIV

<400> SEQUENCE: 11

Gln Leu Leu Leu Asn Gly Ser Leu Ala Glu Glu Glu Ile Val Ile
1               5                   10                  15

<210> SEQ ID NO 12
<211> LENGTH: 15
<212> TYPE: PRT
<213> ORGANISM: HIV

<400> SEQUENCE: 12

Gln Leu Leu Leu Asn Gly Ser Leu Ala Glu Glu Glu Val Val Ile
1               5                   10                  15

<210> SEQ ID NO 13
<211> LENGTH: 14
<212> TYPE: PRT
<213> ORGANISM: HIV

<400> SEQUENCE: 13

Gln Leu Leu Leu Asn Ser Leu Ala Glu Glu Glu Val Val Ile
1               5                   10

<210> SEQ ID NO 14
<211> LENGTH: 27
<212> TYPE: PRT
<213> ORGANISM: artificial sequence
<220> FEATURE:
<223> OTHER INFORMATION: Synthetic peptide

<400> SEQUENCE: 14

Ala Pro Thr Lys Ala Lys Arg Gly Gly Gly Ala Pro Thr Arg Ala Lys
1               5                   10                  15

Arg Gly Gly Gly Ala Pro Thr Glu Ala Lys Arg
            20                  25

<210> SEQ ID NO 15
<211> LENGTH: 26
<212> TYPE: PRT
<213> ORGANISM: artificial sequence
<220> FEATURE:
<223> OTHER INFORMATION: Synthetic peptide

<400> SEQUENCE: 15

Arg Val Val Glu Arg Glu Lys Gly Gly Gly Ala Lys Arg Arg Val Val
1               5                   10                  15

Gly Gly Gly Arg Val Val Gln Arg Glu Lys
            20                  25

<210> SEQ ID NO 16
<211> LENGTH: 24
<212> TYPE: PRT
<213> ORGANISM: artificial sequence
<220> FEATURE:
<223> OTHER INFORMATION: Synthetic peptide

<400> SEQUENCE: 16

-continued

Gly Gly Ala Lys Arg Arg Val Val Gly Gly Ala Lys Arg Arg Val Val
1               5                   10                  15

Gly Gln Arg Glu Lys Arg Ala Val
            20

<210> SEQ ID NO 17
<211> LENGTH: 25
<212> TYPE: PRT
<213> ORGANISM: artificial sequence
<220> FEATURE:
<223> OTHER INFORMATION: Synthetic peptide

<400> SEQUENCE: 17

Cys Gly Gly Ala Lys Arg Arg Val Val Gly Gly Ala Lys Arg Arg Val
1               5                   10                  15

Val Gly Gln Arg Glu Lys Arg Ala Val
            20                  25

<210> SEQ ID NO 18
<211> LENGTH: 23
<212> TYPE: PRT
<213> ORGANISM: artificial sequence
<220> FEATURE:
<223> OTHER INFORMATION: Synthetic peptide

<400> SEQUENCE: 18

Gly Gly Ala Lys Arg Arg Val Val Gly Gly Ala Lys Arg Arg Val Val
1               5                   10                  15

Gly Gly Gln Arg Glu Lys Arg
            20

<210> SEQ ID NO 19
<211> LENGTH: 24
<212> TYPE: PRT
<213> ORGANISM: artificial sequence
<220> FEATURE:
<223> OTHER INFORMATION: Synthetic peptide

<400> SEQUENCE: 19

Cys Gly Gly Ala Lys Arg Arg Val Val Gly Gly Ala Lys Arg Arg Val
1               5                   10                  15

Val Gly Gly Gln Arg Glu Lys Arg
            20

<210> SEQ ID NO 20
<211> LENGTH: 16
<212> TYPE: PRT
<213> ORGANISM: artificial sequence
<220> FEATURE:
<223> OTHER INFORMATION: Synthetic peptide

<400> SEQUENCE: 20

Gly Gly Ala Lys Arg Arg Val Val Gly Gly Ala Lys Arg Arg Val Val
1               5                   10                  15

<210> SEQ ID NO 21
<211> LENGTH: 17
<212> TYPE: PRT
<213> ORGANISM: artificial sequence
<220> FEATURE:
<223> OTHER INFORMATION: Synthetic peptide

<400> SEQUENCE: 21

Gly Cys Gly Ala Lys Arg Arg Val Val Gly Gly Ala Lys Arg Arg Val
1               5                   10                  15

Val

<210> SEQ ID NO 22
<211> LENGTH: 30
<212> TYPE: PRT
<213> ORGANISM: artificial sequence
<220> FEATURE:
<223> OTHER INFORMATION: Synthetic peptide

<400> SEQUENCE: 22

Gly Gly Gly Asp Gln Gln Leu Leu Gly Gly Ala Glu Glu Ile Val
1               5                   10                  15
Gly Gly Ile Glu Glu Glu Gly Gly Glu Arg Asp Arg Asp Arg
            20                  25                  30

<210> SEQ ID NO 23
<211> LENGTH: 31
<212> TYPE: PRT
<213> ORGANISM: artificial sequence
<220> FEATURE:
<223> OTHER INFORMATION: Synthetic peptide

<400> SEQUENCE: 23

Cys Gly Gly Gly Asp Gln Gln Leu Leu Gly Gly Ala Glu Glu Ile
1               5                   10                  15
Val Gly Gly Ile Glu Glu Glu Gly Gly Glu Arg Asp Arg Asp Arg
            20                  25                  30

<210> SEQ ID NO 24
<211> LENGTH: 22
<212> TYPE: PRT
<213> ORGANISM: artificial sequence
<220> FEATURE:
<223> OTHER INFORMATION: Synthetic peptide

<400> SEQUENCE: 24

Gly Gly Asp Gln Gln Leu Leu Gly Gly Ala Glu Glu Glu Ile Val Gly
1               5                   10                  15
Gly Gly Glu Arg Asp Arg
            20

<210> SEQ ID NO 25
<211> LENGTH: 25
<212> TYPE: PRT
<213> ORGANISM: artificial sequence
<220> FEATURE:
<223> OTHER INFORMATION: Synthetic peptide

<400> SEQUENCE: 25

Cys Gly Gly Gly Asp Gln Gln Leu Leu Gly Gly Ala Glu Glu Glu Ile
1               5                   10                  15
Val Gly Gly Ile Glu Glu Glu Gly Gly
            20                  25

<210> SEQ ID NO 26
<211> LENGTH: 15
<212> TYPE: PRT
<213> ORGANISM: artificial sequence
<220> FEATURE:
<223> OTHER INFORMATION: Synthetic peptide

<400> SEQUENCE: 26

Gly Gly Ala Glu Glu Glu Val Val Gly Gly Asp Gln Gln Leu Leu
1               5                   10                  15

<210> SEQ ID NO 27
<211> LENGTH: 16
<212> TYPE: PRT
<213> ORGANISM: artificial sequence
<220> FEATURE:
<223> OTHER INFORMATION: Synthetic peptide

<400> SEQUENCE: 27

Cys Gly Gly Ala Glu Glu Glu Val Val Gly Gly Asp Gln Gln Leu Leu
1               5                   10                  15

<210> SEQ ID NO 28
<211> LENGTH: 25
<212> TYPE: PRT
<213> ORGANISM: artificial sequence
<220> FEATURE:
<223> OTHER INFORMATION: Synthetic peptide

<400> SEQUENCE: 28

Cys Gly Gly Ala Lys Arg Arg Val Val Gly Gly Ala Lys Arg Arg Val
1               5                   10                  15

Val Gly Gln Arg Glu Lys Arg Ala Val
            20                  25

<210> SEQ ID NO 29
<211> LENGTH: 31
<212> TYPE: PRT
<213> ORGANISM: artificial sequence
<220> FEATURE:
<223> OTHER INFORMATION: Synthetic peptide

<400> SEQUENCE: 29

Cys Gly Gly Gly Asp Gln Gln Leu Leu Gly Gly Ala Glu Glu Glu Ile
1               5                   10                  15

Val Gly Gly Ile Glu Glu Glu Gly Gly Glu Arg Asp Arg Asp Arg
            20                  25                  30

<210> SEQ ID NO 30
<211> LENGTH: 24
<212> TYPE: PRT
<213> ORGANISM: artificial sequence
<220> FEATURE:
<223> OTHER INFORMATION: Synthetic peptide

<400> SEQUENCE: 30

Cys Gly Gly Ala Lys Arg Arg Val Val Gly Gly Ala Lys Arg Arg Val
1               5                   10                  15

Val Gly Gly Gln Arg Glu Lys Arg
            20

<210> SEQ ID NO 31
<211> LENGTH: 25
<212> TYPE: PRT
<213> ORGANISM: artificial sequence
<220> FEATURE:
<223> OTHER INFORMATION: Synthetic peptide

<400> SEQUENCE: 31

Cys Gly Gly Gly Asp Gln Gln Leu Leu Gly Gly Ala Glu Glu Glu Ile
1               5                   10                  15

Val Gly Gly Ile Glu Glu Glu Gly Gly
            20                  25

```
<210> SEQ ID NO 32
<211> LENGTH: 16
<212> TYPE: PRT
<213> ORGANISM: artificial sequence
<220> FEATURE:
<223> OTHER INFORMATION: Synthetic peptide

<400> SEQUENCE: 32

Cys Gly Gly Ala Glu Glu Val Val Gly Gly Asp Gln Gln Leu Leu
1               5                   10                  15

<210> SEQ ID NO 33
<211> LENGTH: 18
<212> TYPE: PRT
<213> ORGANISM: artificial sequence
<220> FEATURE:
<223> OTHER INFORMATION: Synthetic peptide

<400> SEQUENCE: 33

Gly Cys Gly Gly Ala Lys Arg Arg Val Val Gly Gly Ala Lys Arg Arg
1               5                   10                  15

Val Val

<210> SEQ ID NO 34
<211> LENGTH: 5
<212> TYPE: PRT
<213> ORGANISM: artificial sequence
<220> FEATURE:
<223> OTHER INFORMATION: Synthetic peptide

<400> SEQUENCE: 34

Asp Gln Gln Leu Leu
1               5

<210> SEQ ID NO 35
<211> LENGTH: 6
<212> TYPE: PRT
<213> ORGANISM: artificial sequence
<220> FEATURE:
<223> OTHER INFORMATION: Synthetic peptide

<400> SEQUENCE: 35

Ala Lys Arg Arg Val Val
1               5

<210> SEQ ID NO 36
<211> LENGTH: 6
<212> TYPE: PRT
<213> ORGANISM: artificial sequence
<220> FEATURE:
<223> OTHER INFORMATION: Synthetic peptide

<400> SEQUENCE: 36

Ala Glu Glu Glu Val Val
1               5

<210> SEQ ID NO 37
<211> LENGTH: 16
<212> TYPE: PRT
<213> ORGANISM: Artificial sequence
<220> FEATURE:
<223> OTHER INFORMATION: Synthetic peptide

<400> SEQUENCE: 37

Gly Gly Ala Ile Val Asn Gly Ser Leu Ala Asp Asp Asp Ile Val Ile
1               5                   10                  15
```

-continued

```
<210> SEQ ID NO 38
<211> LENGTH: 31
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: Cys may be linked to Lys in position 2 in SEQ
      ID NO: 39 or 40 or 42 or 43

<400> SEQUENCE: 38

Gly Ala Lys Arg Arg Val Val Gly Gly Cys Gly Gly Ala Lys Arg Arg
1               5                   10                  15

Val Val Gln Arg Glu Lys Arg Ala Gly Glu Arg Glu Lys Arg Ala
                20                  25                  30

<210> SEQ ID NO 39
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: MUTAGEN
<222> LOCATION: (2)..(2)
<223> OTHER INFORMATION: Lys may be linked to Cys in position 10 in SEQ
      ID NO: 38 or 41

<400> SEQUENCE: 39

Gly Lys Gly Gly Ile Glu Glu Glu Gly Gly Arg Asp Arg Asp Arg Gly
1               5                   10                  15

Gly Glu Gln Asp Arg Asp Arg
                20

<210> SEQ ID NO 40
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Lys may be linked to Cys in position 10 in SEQ
      ID NO: 38 or 41

<400> SEQUENCE: 40

Gly Lys Gly Gly Ile Glu Glu Glu Gly Gly Glu Arg Asp Arg Asp Arg
1               5                   10                  15

Gly Gly Gln Asp Arg Asp Arg
                20

<210> SEQ ID NO 41
<211> LENGTH: 31
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: Cys may be linked to Lys in position 2 in SEQ
      ID NO: 39 or 40 or 42 or 43

<400> SEQUENCE: 41

Gly Ala Lys Arg Arg Val Val Gly Gly Cys Gly Gly Ala Lys Arg Arg
```

```
                 1               5                  10                  15
Val Val Glu Arg Glu Lys Arg Ala Gly Gln Arg Glu Lys Arg Ala
         20                  25                  30

<210> SEQ ID NO 42
<211> LENGTH: 22
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Lys may be linked to Cys in position 10 in SEQ
      ID NO: 38 or 41

<400> SEQUENCE: 42

Gly Lys Gly Gly Ile Glu Glu Glu Gly Gly Gln Asp Arg Asp Arg Gly
 1               5                  10                  15
Gly Arg Asp Arg Asp Arg
         20

<210> SEQ ID NO 43
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Lys may be linked to Cys in position 10 in SEQ
      ID NO: 38 or 41

<400> SEQUENCE: 43

Gly Lys Gly Gly Ile Glu Glu Glu Gly Gly Glu Gln Asp Arg Asp Arg
 1               5                  10                  15
Gly Gly Glu Arg Asp Arg Asp
         20

<210> SEQ ID NO 44
<211> LENGTH: 24
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Trp may be D-Trp
<220> FEATURE:
<221> NAME/KEY: DISULFID
<222> LOCATION: (4)..(10)
<220> FEATURE:
<221> NAME/KEY: MISC_FEATURE
<222> LOCATION: (24)..(24)
<223> OTHER INFORMATION: Carboxyterminal may be amidated

<400> SEQUENCE: 44

Trp Trp Gly Cys Ala Lys Arg Arg Val Cys Gly Gly Ala Lys Arg Arg
 1               5                  10                  15
Val Val Gln Arg Glu Lys Arg Ala
         20

<210> SEQ ID NO 45
<211> LENGTH: 22
<212> TYPE: PRT
<213> ORGANISM: Artificial sequence
```

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Trp may be D-Trp
<220> FEATURE:
<221> NAME/KEY: DISULFID
<222> LOCATION: (4)..(10)
<220> FEATURE:
<221> NAME/KEY: MISC_FEATURE
<222> LOCATION: (22)..(22)
<223> OTHER INFORMATION: Carboxyterminus may be amidated

<400> SEQUENCE: 45

Trp Trp Gly Cys Ile Glu Glu Glu Gly Cys Gly Gly Ile Glu Glu Glu
1               5                   10                  15

Gly Gly Glu Arg Asp Arg
            20

<210> SEQ ID NO 46
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Glu can be Gly
<220> FEATURE:
<221> NAME/KEY: MISC_FEATURE
<222> LOCATION: (5)..(5)
<223> OTHER INFORMATION: Gly can be Arg
<220> FEATURE:
<221> NAME/KEY: MISC_FEATURE
<222> LOCATION: (13)..(13)
<223> OTHER INFORMATION: Arg can be Gln
<220> FEATURE:
<221> NAME/KEY: MISC_FEATURE
<222> LOCATION: (14)..(14)
<223> OTHER INFORMATION: Asp can be Gly
<220> FEATURE:
<221> NAME/KEY: MISC_FEATURE
<222> LOCATION: (15)..(15)
<223> OTHER INFORMATION: Arg can be Lys
<220> FEATURE:
<221> NAME/KEY: MISC_FEATURE
<222> LOCATION: (16)..(16)
<223> OTHER INFORMATION: Asp can be Gly

<400> SEQUENCE: 46

Asp Arg Pro Glu Gly Ile Glu Asn Asn Gly Gly Glu Arg Asp Arg Asp
1               5                   10                  15

Arg

<210> SEQ ID NO 47
<211> LENGTH: 15
<212> TYPE: PRT
<213> ORGANISM: Artificial sequene
<220> FEATURE:
<223> OTHER INFORMATION: Synthetic peptide

<400> SEQUENCE: 47

Ala Pro Thr Lys Ala Lys Arg Arg Val Val Gln Arg Glu Lys Arg
1               5                   10                  15

<210> SEQ ID NO 48
<211> LENGTH: 15
<212> TYPE: PRT
<213> ORGANISM: Artificial sequence
```

```
<220> FEATURE:
<223> OTHER INFORMATION: Synthetic peptide

<400> SEQUENCE: 48

Ala Pro Thr Lys Ala Lys Arg Arg Val Val Glu Arg Glu Lys Arg
1               5                   10                  15

<210> SEQ ID NO 49
<211> LENGTH: 15
<212> TYPE: PRT
<213> ORGANISM: Artificial sequence
<220> FEATURE:
<223> OTHER INFORMATION: Synthetic peptide

<400> SEQUENCE: 49

Ala Pro Thr Arg Ala Lys Arg Arg Val Val Gln Arg Glu Lys Arg
1               5                   10                  15

<210> SEQ ID NO 50
<211> LENGTH: 15
<212> TYPE: PRT
<213> ORGANISM: Artificial sequence
<220> FEATURE:
<223> OTHER INFORMATION: Synthetic peptide

<400> SEQUENCE: 50

Ala Pro Thr Arg Ala Lys Arg Arg Val Val Glu Arg Glu Lys Arg
1               5                   10                  15

<210> SEQ ID NO 51
<211> LENGTH: 15
<212> TYPE: PRT
<213> ORGANISM: Artificial sequence
<220> FEATURE:
<223> OTHER INFORMATION: Synthetic peptide

<400> SEQUENCE: 51

Ala Pro Thr Glu Ala Lys Arg Arg Val Val Glu Arg Glu Lys Arg
1               5                   10                  15

<210> SEQ ID NO 52
<211> LENGTH: 7
<212> TYPE: PRT
<213> ORGANISM: Artificial sequence
<220> FEATURE:
<223> OTHER INFORMATION: Synthetic peptide

<400> SEQUENCE: 52

Ala Pro Thr Lys Ala Lys Arg
1               5

<210> SEQ ID NO 53
<211> LENGTH: 7
<212> TYPE: PRT
<213> ORGANISM: Artificial sequence
<220> FEATURE:
<223> OTHER INFORMATION: Synthetic peptide

<400> SEQUENCE: 53

Ala Pro Thr Arg Ala Lys Arg
1               5

<210> SEQ ID NO 54
<211> LENGTH: 7
<212> TYPE: PRT
<213> ORGANISM: Artificial sequence
<220> FEATURE:
```

-continued

```
<223> OTHER INFORMATION: Synthetic peptide

<400> SEQUENCE: 54

Ala Pro Thr Glu Ala Lys Arg
1               5

<210> SEQ ID NO 55
<211> LENGTH: 7
<212> TYPE: PRT
<213> ORGANISM: Artificial sequence
<220> FEATURE:
<223> OTHER INFORMATION: Synthetic peptide

<400> SEQUENCE: 55

Arg Val Val Glu Arg Glu Lys
1               5

<210> SEQ ID NO 56
<211> LENGTH: 7
<212> TYPE: PRT
<213> ORGANISM: Artificial sequence
<220> FEATURE:
<223> OTHER INFORMATION: Synthetic peptide

<400> SEQUENCE: 56

Arg Val Val Gln Arg Glu Lys
1               5

<210> SEQ ID NO 57
<211> LENGTH: 6
<212> TYPE: PRT
<213> ORGANISM: Artificial sequence
<220> FEATURE:
<223> OTHER INFORMATION: Synthetic peptide

<400> SEQUENCE: 57

Ala Lys Arg Arg Val Val
1               5

<210> SEQ ID NO 58
<211> LENGTH: 15
<212> TYPE: PRT
<213> ORGANISM: Artificial sequence
<220> FEATURE:
<223> OTHER INFORMATION: Synthetic peptide

<400> SEQUENCE: 58

Gln Leu Leu Leu Asn Gly Ser Leu Ala Glu Glu Glu Val Val Ile
1               5                   10                  15

<210> SEQ ID NO 59
<211> LENGTH: 30
<212> TYPE: PRT
<213> ORGANISM: Artificial sequence
<220> FEATURE:
<223> OTHER INFORMATION: Synthetic peptide

<400> SEQUENCE: 59

Cys Gly Gly Gly Asp Gln Gln Leu Leu Gly Gly Ala Glu Glu Glu Ile
1               5                   10                  15

Val Gly Gly Ile Glu Glu Glu Gly Gly Glu Arg Asp Arg Asp
            20                  25                  30

<210> SEQ ID NO 60
<211> LENGTH: 25
<212> TYPE: PRT
```

```
<213> ORGANISM: Artificial sequence
<220> FEATURE:
<223> OTHER INFORMATION: Synthetic peptide

<400> SEQUENCE: 60

Gly Ala Lys Arg Arg Val Val Gly Gly Cys Gly Gly Ala Lys Arg Arg
1               5                   10                  15

Val Val Gln Arg Glu Lys Arg Ala Gly
            20                  25

<210> SEQ ID NO 61
<211> LENGTH: 5
<212> TYPE: PRT
<213> ORGANISM: Artificial sequence
<220> FEATURE:
<223> OTHER INFORMATION: Synthetic peptide

<400> SEQUENCE: 61

Arg Glu Lys Arg Ala
1               5
```

STABILIZED HIV-1 PEPTIDE CONSTRUCTS COMPRISING THE GP120 C5 DOMAIN AND GP41 HYDROPHILIC DOMAIN

REFERENCE TO SEQUENCE LISTING SUBMITTED ELECTRONICALLY

The content of the electronically submitted sequence listing in ASCII text file (Name: "2675_0020003_SeqListing.txt"; Size: 15,000 bytes; and Date of Creation: Nov. 17, 2015) filed herewith is incorporated herein by reference in its entirety.

FIELD OF THE INVENTION

The present invention relates to novel agents and methods for treatment, diagnosis and prognosis of HIV infection and AIDS and the invention further relates to methods for identifying and providing agents useful for the treatment and diagnosis.

In particular, the present invention relates to novel therapeutic agents which can effect stabilisation of a complex between domains in certain HIV proteins and to diagnostic and prognostic agents useful for demonstrating the presence of such agents.

BACKGROUND OF THE INVENTION

In recent years a large body of research evidence has accumulated supporting the concept that AIDS is an immunological disease induced by HIV-1 rather than simply being caused by loss of CD4+T-lymphocytes as a result of chronic cytopathic viral infection. It is therefore important to develop interventions that also target the chronic immune stimulation induced by HIV-1.

Previous research shows that antibodies to the carboxyterminal C5 domain of HIV-1 gp120 has been associated with lower immune activation and slower disease progression (Loomis-Price et al. 1998 J. Inf Dis. 178:1306-1316; Warren R Q wt al. 1991 J. Clin Immunol 11: 13-21; Lifson et al. 1991 J. Inf. Dis 163:959-965). Indeed, disease progression was shown to accelerate if humoral (i.e antibody) responses to this domain were lost (Wong et al. 1993 J. Inf. Dis 168: 1523-1527). Furthermore long term nonprogressors (LTNP) which represent 5% of HIV-infected individuals have sustained humoral responses to the carboxyterminal C5 domain of HIV-1 gp120 and can live in the absence of antiretroviral therapy for many years despite having some degree of viral load (Liegler et al. 1998 J. Infec. Dis. 178: 669-79; Gougeon et al. 1996 J. Immuno) 156:3509-20; Muro-Cacho et al. 1995 J. Immunol 154:5555-66; Easterbrook et al. 1999 J. Infect 28:71-73).

The C5 domain of gp120 is 13 amino acids long (amino acid residues 499-511 of gp120, and has the reference sequence B.FR 83.HXB2-TKAKRRVVQREKR). Its conservation across multiple virus clades is shown in Table 1. The only regions that show any substantial variation are at positions 500 and 507 of the sequence which may contain predominantly amino acids K, R and E at position (500) or predominantly Q, E at position (506).

TABLE 1

(C5-domain for different multiple clades)

| C5 SEQUENCES Residues 497-511 | VIRAL CLADES (%) | | | | | |
|---|---|---|---|---|---|---|
| | A | A1 | A2 | B | C | D |
| APTKAKRRVVQREKR (SEQ ID NO: 47) | 3.1% | / | / | 58.3% | 0.7% | / |
| APTKAKRRVVEREKR (SEQ ID NO: 48) | 21.9% | 12.8% | / | / | 23.5% | 33.0% |
| APTRAKRRVVQREKR (SEQ ID NO: 49) | 3.1% | / | / | 12.4% | / | 1.7% |
| APTRAKRRVVEREKR (SEQ ID NO: 50) | 15.6% | 27.7% | 33.3% | / | 3.0% | 33.3% |
| APTEAKRRVVEREKR (SEQ ID NO: 51) | / | / | / | / | 16.8% | 3.3% |
| | 43.7% | 40.5% | 33.3% | 70.7% | 44.0% | 68.3% |

The table provided is based on 1066 sequences downloaded from the Los Alamos HIV-database 3rd of May 2008.

The sequences grouped in the following viral clades:

A: 32 sequences, A1: 47 sequences, A2: 10 sequences, B: 453 sequences, C: 464 sequences, and D: 60 sequences.

This carboxyterminal constant region C5 of HIV-1 gp120 is immunodominant and highly conserved across multiple HIV subtypes. It is exposed on the 3D structure of native gp120, on virions and on cell surface expressed gp120. Indeed, the C5 domain resembles human leukocyte antigen (HLA) classes I and II molecules and has the ability to bind peptides and deletion of the C5 domain abrogates peptide binding (Cadogan et al. AIDS Research and Human Retorviruses (2008); Vol. 24: 845-855). In this way the C5 domain can mimic the activities of human HLA.

However, to date the mechanisms behind C5-associated immune activation are currently largely unknown, meaning that it has been impossible to rationally devise drugs and diagnostic/prognostic means based on these mechanisms.

OBJECT OF THE INVENTION

It is an object of embodiments of the invention to provide agents and methods which can be used in the prevention and/or treatment and/or diagnosis and/or prognosis of HIV infection and AIDS.

SUMMARY OF THE INVENTION

It has been found by the present inventor(s) that peptide constructs ("peptide combinations") composed of amino acid sequences from the C5 domain of gp120 and of amino acid sequences from the transmembrane domain of gp41 are recognized by antisera isolated from a large fraction of LTNP (long-term non-progressing) HIV infected subjects, whereas the same constructs are substantially not recognized by antisera from subjects not infected with HIV or antisera from non-LTNP HIV-infected subjects. Similar results have been observed for peptide constructs composed of C5 and C2 derived peptide hybrids.

In particular, testing for antibodies in HIV longterm nonprogressors (LTNP) with novel antigens comprising amino acid sequences of the C5 domain combined with various other amino acid sequences found on gp160 outside the C5 domain have shown new and surprising properties. This combination of amino acid sequences is useful for identifying a set of antibody responses unique for HIV infected individuals that despite the infection show no signs of disease progression. Similar antigens that incorporate cross clade viral variation will be used to induce broad anti-C5 and anti C5:CX (meaning an association between C5 and a non-C5 region in gp41 or gp120) humeral responses equivalent to those found in longterm nonprogressor/elite controllers.

It is therefore concluded herein that the LTNP state characterizing 5% of HIV-infected individuals is at least partly a consequence of the ability of these infected individuals to develop antibodies against conformational epitopes composed of amino acids from both C5 and from TM-gp41 or C2. Such antibodies will, due to their binding to both C5 and to TM-gp41 or C2, stabilise a specific conformation where C5 is complexed to tm-gp41 and/or C2. Consequently, this opens for the development and production of novel antibodies which share the same specificity as do the antibodies identified herein, but it also opens for the development of immunogenic agents which will be capable of inducing antibodies which can stabilise the complex formation between C5 and TM-gp41 on the one hand or C5 and C2 on the other hand.

Peptide antigens to the carboxyterminal C5 domain of the HIV-1 envelope glycoprotein gp120 conjugated or complexed (CX) to regions on the transmembrane gp41 and/or constant domain C2 of gp120 can be used as vaccine agents for eliciting antibody immune responses to prevent/suppress chronic immune stimulation associated with C5 in HIV infected individuals. Peptide antigens to these domains can also be used within diagnostics and prognostics for the identification of such antibodies in HIV-infected individuals to determine whether they may be longterm nonprogressor patients, or whether they are candidates for vaccination. The test could also be used to determine whether vaccination has been successful.

Since this invention provides a novel mechanism for C5-associated immune activation, this also highlights the potential for other molecules than antibodies to stabilise interactions with C5 and gp41 and/or C2 to prevent availability of free C5 that can lead to C5-associated immune activation.

The C5 domain of HIV-1 gp120 may be associated with immune activation in a number of ways:
1) C5 may be presented as a peptide on different HLA molecules on infected cells. The variation of positions 500 and 507 indicate a plasticity to interact with multiple HLA molecules.
2) C5 can bind peptide and function as an HLA molecule to interact with T-Cell receptors. Other molecules involved in interaction with the TCR complex are present on the cell surface or incorporated into the virus particle. Cadogan et al. 2008 AIDS Res and Hum Retroviruses 24:845-55.

As noted this opens for several new ways of targeting the immune activation exerted by HIV:

If C5 is stabilised by remaining bound/complexed to gp41 and/or C2, C5 would remain inert/inactive. C5 therefore appears to vacillate between binding to gp41 and C2. On the other hand, when C5 is disengaged from either gp41 or C2 it can lead to immune activation.

It should therefore be possible to block C5 associated immune activation in a number of ways, which are all contemplated according to the present invention:

Peptide combinations comprising peptides from C5 in interaction with gp41 and C2 mimic the in vivo complex between C5 and gp41 or C2 and will be able to induce antibody responses against the native complex. These antibodies can in turn block C5 associated immune activation by "locking" C5 conformationally.

Also, small molecules that block disengagement of C5 and keep it stable with gp41 or C2 (in a manner similar to the antibodies induced by the peptide combinations) or small molecules or antibodies that bind the free C5 and thereby render it inert and block immune activation. For instance, small molecules corresponding to regions of C2 and gp41 that interact with C5 can be used to inhibit this C5-associated immune activation.

Vaccines based on the C5 domain of HIV-1 complexed/conjugated to domains of gp41 and/or C2 are different from conventional antibody approaches to HIV vaccines since the antibodies to be induced are generally non-neutralising. Other approaches to HIV vaccines involve larger antigens that have addressed the entire gp120, gp41 or the uncleaved precursor gp160. However, they have not addressed the regions of the C5 domain specifically complexed with gp41 and/or C2.

So, in a first aspect of the present invention is provided a method for reducing and/or delaying pathological effects of human immunodeficiency virus I (HIV) in a human infected with HIV, the method comprising administering an effective amount of one or more agents capable stabilising association of the C5 domain of HIV gp120 with the transmembrane domain of gp41 and/or with the constant C2 domain of gp120.

In a second aspect is provided a method for reducing and/or delaying pathological effects of human immunodeficiency virus I (HIV) in a human infected with HIV, the method comprising administering an effective amount of one or more immunogens, which induces antibodies that stabilise association of the C5 domain of HIV gp120 with the transmembrane domain of gp41 and/or with the constant C2 domain of gp120.

In a third aspect is provided a method of reducing the risk of developing acquired immunodeficiency syndrome (AIDS) or HIV disease, the method comprising administering an effective amount of one or more immunogens, which induces antibodies that stabilises association of the C5 domain of HIV gp120 with the transmembrane domain of gp41 and/or with the constant C2 domain of gp120.

In a fourth aspect is provided a method of reducing the risk of developing acquired immunodeficiency syndrome (AIDS), the method comprising administering an effective amount of an agent capable of stabilising association of the C5 domain of HIV gp120 with the transmembrane domain of gp41 and/or with the constant C2 domain of gp120.

In a fifth aspect is provided a peptide combination, said combination comprising a first peptide comprising the amino acid sequence of the 13 amino acid residue amino acid sequence of the C5 domain of HIV gp120 including between 0 and 4 amino acid substitutions, a subsequence thereof, or an amino acid sequence comprising the inverso-, retro- or retro-inverso form of said amino acid sequence or subsequence, and at least one second peptide having an amino acid stretch present in the transmembrane domain of gp41 or present in the constant C2 domain of gp120 or having an amino acid stretch present in any one of SEQ ID NOs. 6-13 or having a inverso-, retro- or retro-inverso form of an amino acid stretch present in the transmembrane domain of gp41 or present in the constant C2 domain of gp120, wherein said peptide combination is capable of inducing an antibody which can bind and stabilise the association of the C5 domain of HIV gp120 with the transmembrane domain of gp41 and/or with the constant C2 domain of gp120, and wherein said peptide combination lacks amino acids N-terminal of C5 in gp120.

In a sixth aspect is provided an immunogenic composition comprising a peptide combination of the present invention in combination with a pharmaceutically acceptable diluent or vehicle and optionally an immunological adjuvant.

In a seventh aspect is provided a nucleic acid fragment encoding a peptide combination, said peptide combination comprising a first peptide which is identical to the first peptide of a peptide combination of the present invention, with the proviso that the amino acid residues in said first peptide are L-forms selected from the group consisting of Ala, Cys, Asp, Glu, Phe, Gly, His, Ile, Lys, Leu, Met, Asn, Pro, Gln, Arg, Ser, Thr, Val, Trp, and Tyr, and at least one second peptide which is identical to a second peptide of a peptide combination of the present invention, with the proviso that the amino acid residues in said second peptide are L-forms, wherein said peptide combination is capable of inducing an antibody which can bind and stabilise the association of the C5 domain of HIV gp120 with the transmembrane domain of gp41 and/or with the constant C2 domain of gp120, and wherein said peptide combination lacks amino acids N-terminal of C5 in gp120.

In a eighth aspect is provided a vector comprising a nucleic acid fragment of the invention.

In a ninth aspect is provided an immunogenic composition comprising a nucleic acid fragment or vector of the present invention, in combination with a pharmaceutically acceptable diluent or vehicle and optionally an immunological adjuvant.

In a tenth aspect is provided a method for determining the presence of antibodies which bind an epitope composed of amino acids in the C5 domain of gp120 as well as of amino acids in the transmembrane domain of gp41 and/or the constant C2 domain of gp120, the method comprising contacting a sample potentially comprising said antibodies with at least one peptide combination according of the present invention, and determining quantitatively or qualitatively binding between said at least one peptide combination and antibodies in said sample.

In an eleventh aspect is provided a kit for determining the presence of antibodies which bind an epitope composed of amino acids in the C5 domain of gp120 as well as of amino acids in the transmembrane domain of gp41 and/or the constant C2 domain of gp120, the kit comprising at least one peptide combination of the invention, means for reacting a liquid sample with said peptide combination, and means for determining the presence of a positive or negative binding reaction between antibodies and said peptide combination.

In a twelfth aspect is provided a method for isolating agents capable of stabilising association of the C5 domain of HIV gp120 with the transmembrane domain of gp41 and/or with the constant C2 domain of gp120, the method comprising testing candidate agents for their ability to displace a reference agent, which has previously established to be capable of stabilising said association, from its stabilising binding to said C5 domain and to said transmembrane domain of gp41 and/or said C2 domain or from its binding to a surrogate of said C5 domain and of said transmembrane domain and/or said C2 domain, and isolating those candidate agents which are capable of displacing said reference agent, or testing candidate agents for their ability to bind to a surrogate of a complex between the C5 domain and the transmembrane domain of gp41 and/or the C2 domain of gp120 and isolating those agents which are capable of exerting significant binding to said surrogate.

In a thirteenth aspect is provided an analogue of the C5 domain of gp120, comprising the amino acid sequence having formula II $$Y^1\text{-}Y^2\text{-}Y^3\text{-}Y^4\text{-}Y^5\text{-}Y^6\text{-}Y^7\text{-}Y^8\text{-}Y^9\text{-}Y^{10}\text{-}Y^{11}\text{-}Y^{12}\text{-}Y^{13} \quad (II)$$

wherein $Y^1$ is Thr, $Y^2$ is selected from Lys, Arg, Har (homoarginine), and Glu, $Y^3$ is selected from Ala and Val, $Y^4$ is selected from Arg, Lys, Har and Cit (citrulline), $Y^5$ is selected from Arg, Lys, Har and Cit, $Y^6$ is selected from Arg, Har, Lys and Cit, $Y^7$ is selected from Val, Leu, Ile and Nle (norleucin), $Y^8$ is selected from Val, Leu Ile and Nle, $Y^9$ is selected from Gln, Glu, Asn and Asp, $Y^{10}$ is selected from Arg, Har and Cit, $Y^{11}$ is selected from Glu and Asp, $Y^{12}$ is Lys, and $Y^{13}$ is selected from Arg, Har and Cit, and wherein $Y^3$ is Val and/or wherein $Y^4$ is selected from Arg, Har and Cit and/or wherein
$Y^5$ is selected from Lys and Cit and/or wherein
$Y^6$ is selected from Lys and Cit and/or wherein
$Y^7$ is selected from Leu, Ile and Nle and/or wherein
$Y^8$ is selected from Leu Ile and Nle and/or wherein
$Y^9$ is selected from Glu, Asn and Asp and/or wherein
$Y^{10}$ is Cit or $Y^{11}$ is Asp or $Y^{13}$ is Cit or comprises a subsequence of at least 6 amino acid residues of the amino acid sequence of formula II, or comprises the inverso-, retro- or retro-inverso form of said amino acid sequence or subsequence.

LEGENDS TO THE FIGURE

FIG. 1: Combined histogram and line plot. The line plot shows ratios between measured OD values for peptide solution A (SEQ ID NO: 47 alone) and B (SEQ ID NOs 47 and 6), and the histogram shows average responses within each ratio interval for SEQ ID NO: 47. Error bars are calculated as stdev/square root of n. See Example 4 for details.

Figure 2:
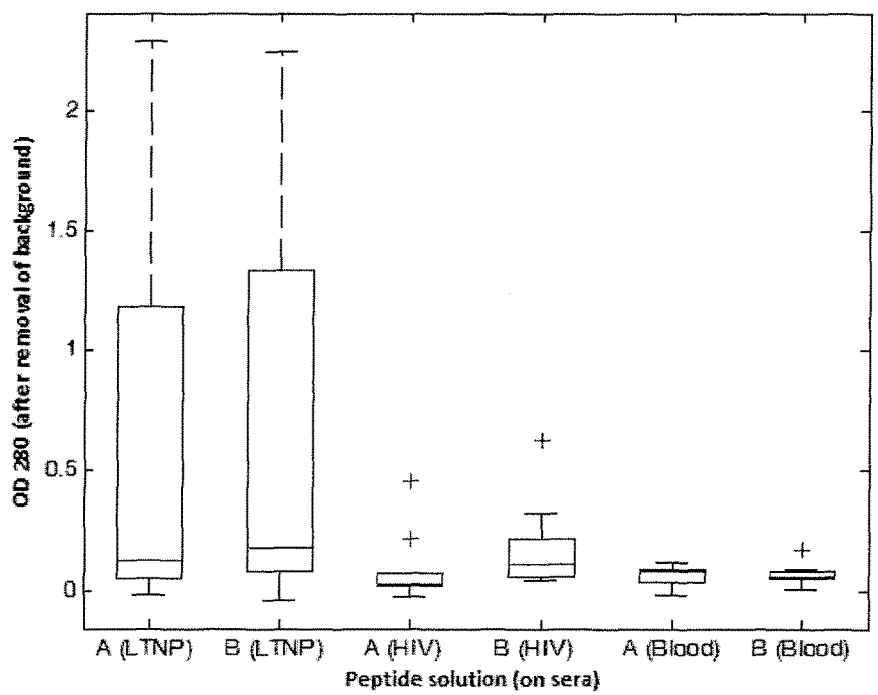

FIG. 2: Comparing responses to A (SEQ ID NO: 47 alone) and B (SEQ ID NO: 47 combined with SEQ ID NO: 6) in different groups of subjects (LTNP, HIV positives, and blood donors). Boxes indicate interquartile range. Median value is indicated by a horizontal line. The lines extending from each end of the box=1.5 lengths in unit of interquartile range. Crosses=Values beyond the ends of the lines.

Figure 3:
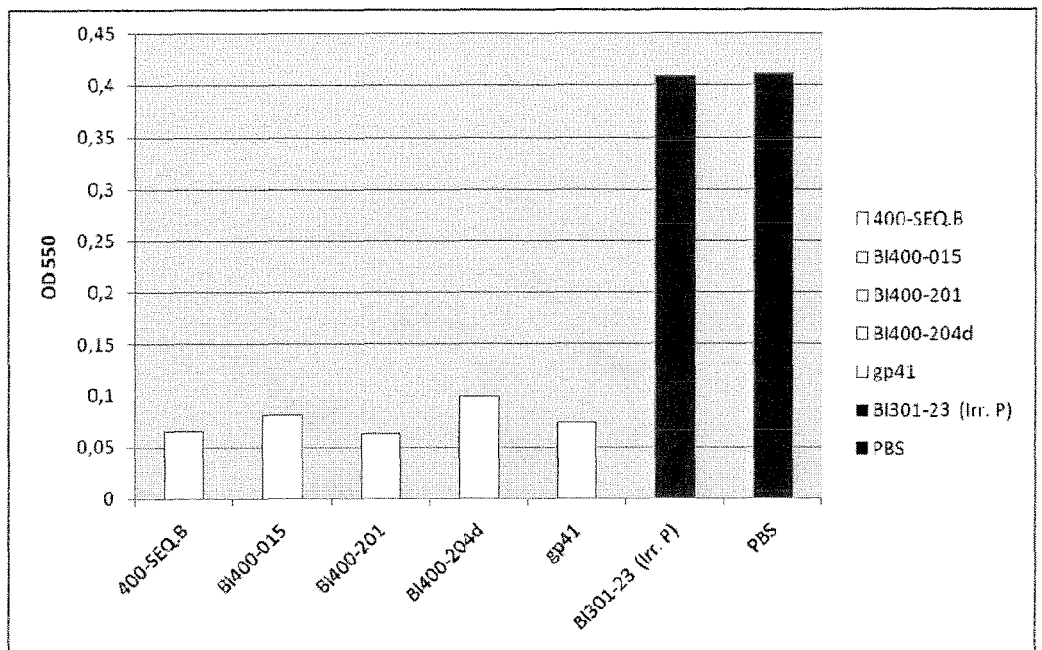

FIG. 3: Inhibition of antibody binding using different antigens.

Antigens used: BI400-B, C5 (BI400-015), gp41 peptide (BI400-201), C2 peptide (BI400-201d), recombinant gp41. BI301-23 is an irrelevant peptide unrelated to HIV, PBS is phosphate buffered saline without any peptide antigen. See Example 5 for details.

Figure 4:
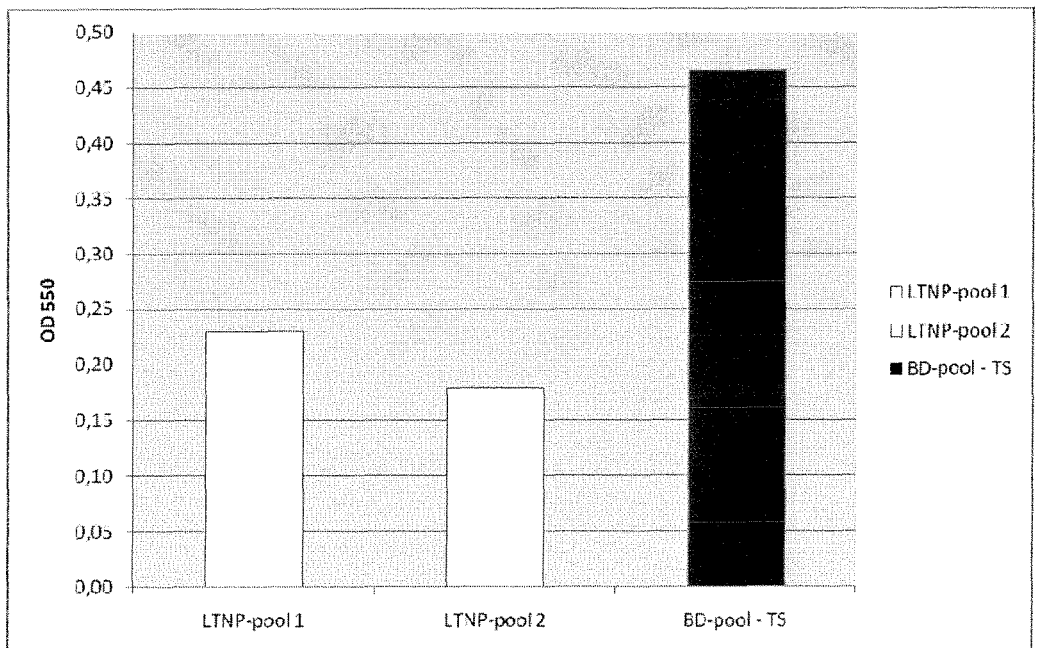

FIG. 4: Cross competition of BI400-B antibody binding to C5/gp41 using serum from LTNP. LTNP-pool 1 is a pool consisting of sera collected from five defined LTNP patients. LTNP-pool 2 is a pool consisting of sera collected from four other defined LTNP patients. BD pool is a pool consisting of 10 sera from healthy blood donors.

Figure 5:
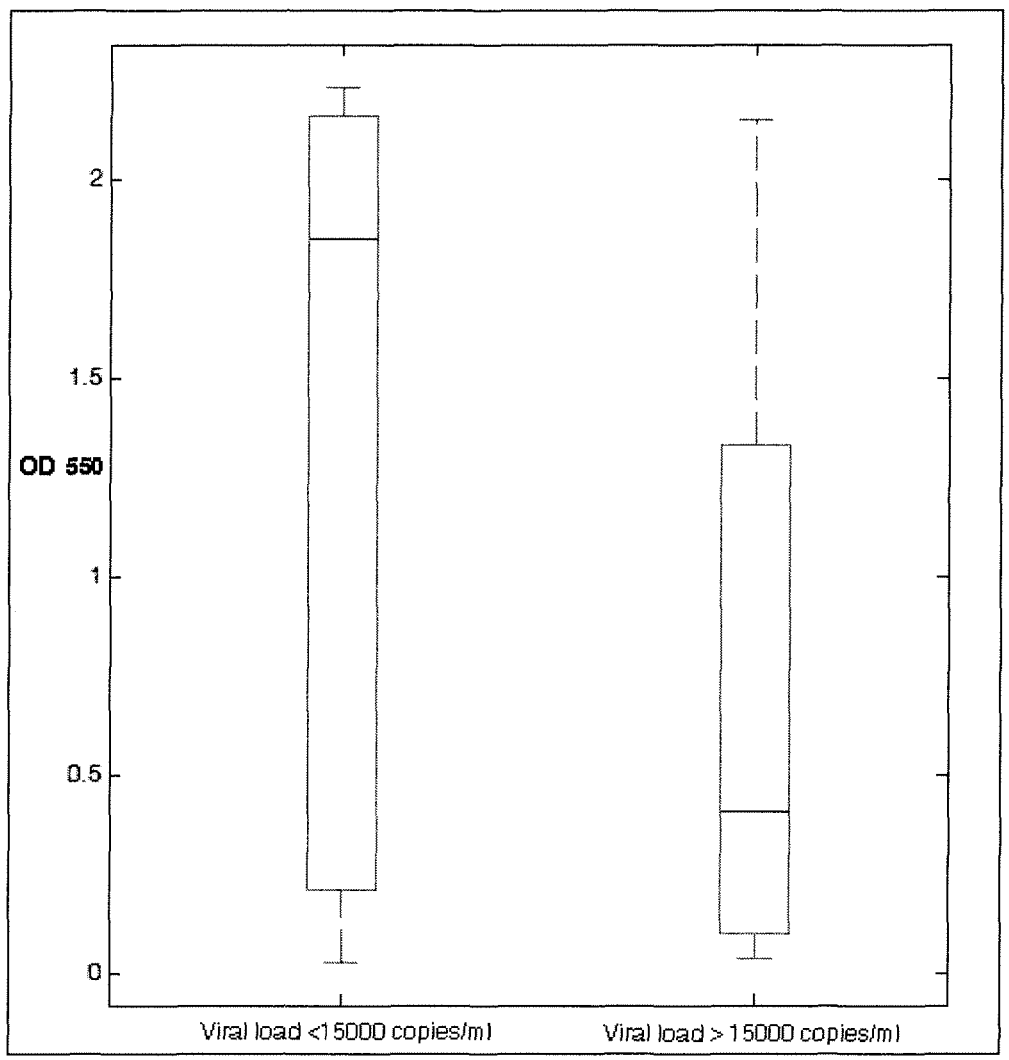

FIG. 5: Prevalence of anti-05/gp41 antibodies in HIV infected individuals varies according to viral load.

Boxes indicate interquartile range. The median value is indicated by a horizontal line. The lines extending from each end of the box=1.5 lengths in unit of interquartile range. See Example 5 for details.

DETAILED DISCLOSURE OF THE INVENTION

Definitions

When terms such as "one", "a" or "an" are used in this disclosure they mean "at least one", or "one or more" unless otherwise indicated. Further, the term "comprising" is intended to mean "including" and thus allows for the presence of other constituents, features, conditions, or steps than those explicitly recited.

"HIV" generally denotes human immunodeficiency virus I.

"HIV disease" is composed of several stages including the acute HIV infection which often manifests itself as a flu-like infection and the early and medium stage symptomatic disease, which has several non-characteristic symptoms such as skin rashes, fatigue, night sweats, slight weight loss, mouth ulcers, and fungal skin and nail infections. Most HIV infected will experience mild symptoms such as these before developing more serious illnesses. It is generally believed that it takes five to seven years for the first mild symptoms to appear. As HIV disease progresses, some individuals may become quite ill even if they have not yet been diagnosed with AIDS (see below), the late stage of HIV disease. Typical problems include chronic oral or vaginal thrush (a fungal rash or spots), recurrent herpes blisters on the mouth (cold sores) or genitals, ongoing fevers, persistent diarrhea, and significant weight loss. "AIDS" is the late stage HIV disease and is a condition which progressively reduces the effectiveness of the immune system and leaves individuals susceptible to opportunistic infections and tumors.

When using the term "gp120" herein is meant the ≈120 kDa N-terminal glycoprotein enzymatic cleavage product of gp160, which in turn is the sole expression product of the HIV env gene. gp120 forms the "spikes" on infective HIV virions and is non-covalently bound to gp41.

"gp41" denotes the ≈41 kDa glycoprotein C-terminal enzymatic cleavage product of gp160. gp41 is located intracellularly in HIV infected cells or inside the viral capsid in infective HIV virions. gp41 has an N-terminal transmembrane domain which binds non-covalently to gp120. This transmembrane domain is termed "the transmembrane domain of gp41" or "tm-gp41" herein. The term includes within its scope naturally occurring mutated versions of the sequence as e.g. those set forth in Formula III.

"C5" or the "C5 domain" denotes the 13 C-terminal amino acid residues of gp120.

"C2" or the "C2 domain" denotes a conserved region in gp120. Regions in C2 form an antiparallel β-sheet with C5 in the inner proximal domain of gp120.

"Reducing and/or delaying pathological effect of HIV" is in the present context meant to denote that use of the methods of the invention provides for a statistically significant reduction and/or delay in morbidity seen in individual infected with HIV which are treated according to the present invention. That is, the time of onset of manifest disease symptoms characterizing AIDS is later compared to non-treated controls and/or the number of pathological manifestations is reduced to controls not receiving the treatment of the present invention.

The expression "association of the C5 domain of HIV gp120 with the transmembrane domain of gp41 and/or with the constant C2 domain of gp120" means that C5 can interacting non-covalently with both or one of the tm-g41 and C2. The interaction with tm-gp41 is intermolecular, whereas the interaction with C2 is intramolecular.

An "agent capable of stabilising" association of the C5 domain of HIV gp120 with the transmembrane domain of gp41 and/or with the constant C2 domain of gp120 is a composition of matter which prevents or statistically reduces release of C5 from its intermolecular binding to gp41 and/or from its intramolecular binding to C2. Generally, such an agent is any substance of matter capable of exerting this effect, but important examples are antibodies, antibody fragments, and antibody analogues. However, also other molecules having proper binding affinity for a complex between C5 on the one hand and tm-gp41 and/or C2 on the other, is an agent according the present invention—the precise molecular format is less important than the binding characteristics, and it is according to the invention also possible that such an agent may be a receptor or a receptor analogue, but also small molecule stabilisers are capable of functioning as an agent of the present invention.

The term "antibody" herein is used in the broadest sense and specifically includes full-length monoclonal antibodies, polyclonal antibodies, multispecific antibodies (e.g., bispecific antibodies), and antibody fragments, so long as they exhibit the desired biological activity, i.e. to function as an agent described above. Various techniques relevant to the production of antibodies are provided in, e.g., Harlow, et al., Antibodies: A Laboratory Manual, Cold Spring Harbor Laboratory Press, Cold Spring Harbor, N.Y., (1988).).

An "antibody fragment or antibody analogue" comprises a portion of a full-length antibody, preferably antigen-binding or variable regions thereof. Examples of antibody fragments/analogues include Fab, Fab', $F(ab)_2$, $F(ab')_2$, $F(ab)_3$, Fv (typically the VL and VH domains of a single arm of an antibody), single-chain Fv (scFv), dsFv, Fd fragments (typically the VH and CH1 domain), and dAb (typically a VH domain) fragments; VH, VL, VhH, and V-NAR domains; minibodies, diabodies, triabodies, tetrabodies, and kappa bodies (see, e.g., Ill et al., Protein Eng 1997; 10: 949-57); camel IgG; IgNAR; and multispecific antibody fragments formed from antibody fragments, and one or more isolated CDRs or a functional paratope, where isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23; 1126-1136; WO2005040219, and published U.S. Patent Applications 20050238646 and 20020161201.

The term "antibody derivative", as used herein, comprises a full-length antibody or a fragment of an antibody, preferably comprising at least antigen-binding or variable regions thereof, wherein one or more of the amino acids are chemically modified, e.g., by alkylation, PEGylation, acylation, ester formation or amide formation or the like, e.g., for linking the antibody to a second molecule. This includes, but is not limited to, PEGylated antibodies, cysteine-PEGylated antibodies, and variants thereof.

A "conjugate" as used herein comprises an agent according to the invention such as an antibody derivative associated with or linked to a second agent, such as a cytotoxic agent, a detectable agent, etc. A conjugate may be constituted of covalently linked peptides (an example of a conjugate is a fusion peptide comprising two peptides linked via peptide bonds so that the conjugate in that case may be an expression product from a nucleic acid fragment), but a conjugate can also be a combination of peptides covalent linked via chemical conjugation (a traditional example is conjugation using glutaraldehyde). Another example of a more complex conjugation is the example where an agent or peptide combination or other chemical substance of the present invention is linked to a carrier molecule, which in turn i coupled to other agents, peptide combinations or other chemical substances of the present invention (e.g. when such chemical substances are bound to a poly-lysine carrier (a lysine "tree")).

A "humanized" antibody is a human/non-human chimeric antibody that contains a minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody can optionally also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992), WO 92/02190, US Patent Application 20060073137, and U.S. Pat. Nos. 6,750,325, 6,632,927, 6,639,055, 6,548,640, 6,407,213, 6,180,370, 6,054,297, 5,929,212, 5,895,205, 5,886,152, 5,877,293, 5,869,619, 5,821,337, 5,821,123, 5,770,196, 5,777,085, 5,766,886, 5,714,350, 5,693,762, 5,693,761, 5,530,101, 5,585,089, and 5,225,539.

An antibody having a "biological characteristic" of a reference antibody, is one that possesses one or more of the biological characteristics of that antibody that distinguish it from other antibodies that bind to the same antigen.

The term "peptide" is in the present context intended to mean both short peptides of from 2 to 10 amino acid residues, oligopeptides of from 11 to 100 amino acid residues, and polypeptides of more than 100 amino acid residues. When referring to amino acids in peptides, it is intended that the amino acids are L-amino acids, unless other information is provided.

A "protein" is intended to denote a functional biomolecule comprising at least one peptide; when comprising at least two peptides, these may form complexes, be covalently linked, or may be non-covalently linked. The polypeptide(s) in a protein can be glycosylated and/or lipidated and/or comprise prosthetic groups.

A "peptide combination" denotes a molecule which is constituted by at least two peptides in a non-natural configuration relative to each other. Examples are peptides from the same or from different proteins which are covalently linked via the side chains of at least one of their amino acids, or which are linked via their termini (e.g. via peptide bonds) but in a configuration which does not appear in nature. Typical examples of peptide combinations are detailed below.

A "variant" or "analogue" of a peptide refers to a peptide having an amino acid sequence that is substantially identical to a reference peptide, typically a native or "parent" polypeptide. The peptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). A particular form of conservative amino acid substitutions include those with amino acids, which are not among the normal 20 amino acids encoded by the genetic code. Since preferred embodiments of the present invention entail use of synthetic peptides, it is unproblematic to provide such "non-naturally occurring" amino acid residues in the peptides disclosed herein, and thereby it is possible to exchange the natural saturated carbon chains in the side chains of amino acid residues with shorter or longer saturated carbon chains—for instance, lysine may be substituted with an amino acid having an the side chain—$(CH_2)_nNH_3$, where n is different from 4, and arginine may be substituted with an amino acid having the side chain —$(CH_2)_nNHC(=NH_2)NH_2$, where n is different from 3, etc. Similarly, the acidic amino acids aspartic acid and glutamic acid may be substituted with amino acid residues having the side chains —$(CH_2)_nCOOH$, where n>2.

A "retro form" of a peptide is a form of a peptide where the order of the amino acids in N- to C-terminal direction has been inverted. For instance, the retro form of ALDFR is the peptide RFDLA.

An "inverso" form is characterized by the fact that each amino acid in the inverso form is in the opposite stereochemical configurational compared to the corresponding amino acid in the peptide. So, if the peptide is composed of L-amino acids, the inverso form is composed of D-amino acids.

A "retro-inverso" form of a peptide is a form of a peptide which is both an inverso form and a retro form. The retro-inverso form of L-ala-L-Arg-L-Lys is D-Lys-D-Arg-D-ala.

The term "substantially identical" in the context of two amino acid sequences means that the sequences, when optimally aligned, such as by the programs GAP or BEST-FIT using default gap weights, share at least about 50, at least about 60, at least about 70, at least about 80, at least about 90, at least about 95, at least about 98, or at least about 99 percent sequence identity. In one embodiment, residue positions that are not identical differ by conservative amino acid substitutions. Sequence identity is typically measured using sequence analysis software. Protein analysis software matches similar sequences using measures of similarity assigned to various substitutions, deletions and other modifications, including conservative amino acid substitutions. For instance, the publicly available GCG software contains programs such as "Gap" and "BestFit" which can be used with default parameters to determine sequence homology or sequence identity between closely related polypeptides, such as homologous polypeptides from different species of organisms or between a wild-type protein and a mutein thereof. See, e.g., GCG Version 6.1. Polypeptide sequences can also be compared using FASTA or ClustalW, applying default or recommended parameters. A program in GCG Version 6.1., FASTA (e.g., FASTA2 and FASTA3) provides alignments and percent sequence identity of the regions of the best overlap between the query and search sequences (Pearson, Methods Enzymol. 1990; 183:63-98; Pearson, Methods Mol. Biol. 2000; 132:185-219). Another preferred algorithm when comparing a sequence to a database containing a large number of sequences from various organisms, or when deducing the is the computer program BLAST, especially blastp, using default parameters. See, e.g., Altschul et al., 3. Mol. Biol. 1990; 215:403-410; Altschul et al., Nucleic Acids Res. 1997; 25:3389-402 (1997); each herein incorporated by reference. "Corresponding" amino acid positions in two substantially identical amino acid sequences are those aligned by any of the protein analysis software mentioned herein, typically using default parameters.

The term "subsequence" in general means any consecutive stretch of at least 3 amino acids or, when relevant, of at least 3 nucleotides, derived directly from a naturally occurring amino acid sequence or nucleic acid sequence, respectively. However, when discussing peptide combinations of the present invention, the subsequence may be as short as 1 or 2 amino acids. This is because the inventive peptide combinations include amino acids from different peptide domains, where the amino acids together at least form a conformational epitope for an antibody. Hence, such a conformational epitope could be composed of 4 amino acids from C5, but only 1 or 2 from tm-gp41—the important point is here that this combined epitope from 2 domains is capable of being stabilised, i.e. that antibody binding to the same epitope in vivo will stabilise the configuration between C5 and tm-gp41 and/or C2.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome-binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of an antibody molecule will exhibit 98%-99% homogeneity for antibody molecules in the context of all present peptide species in the composition or at least with respect to substantially active peptide species in the context of proposed use.

In the context of the present invention, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

The term antigen denotes a substance of matter which is recognized by the immune system's specifically recognizing components (antibodies, T-cells).

The term "immunogen" is in the present context intended to denote a substance of matter, which is capable of inducing an adaptive immune response in an individual, where said adaptive immune response targets the immunogen. In relation to the present invention, an immunogen will induce antibodies that react with the immunogen. In other words, an immunogen is an antigen, which is capable of inducing immunity.

The terms "epitope", "antigenic determinant" and "antigenic site" are used interchangeably herein and denotes the region in an antigen or immunogen which is recognized by antibodies (in the case of antibody binding epitopes, also known as "B-cell epitopes") or by T-cell receptors when the epitope is complexed to an MHC molecule (in the case of T-cell receptor binding epitopes, i.e. "T-cell epitopes").

The term "immunogenically effective amount" has its usual meaning in the art, i.e. an amount of an immunogen, which is capable of inducing an immune response, which significantly engages pathogenic agents, which share immunological features with the immunogen.

The term "vaccine" is used for a composition comprising an immunogen and which is capable of inducing an immune response which is either capable of reducing the risk of developing a pathological condition or capable of inducing a therapeutically effective immune response which may aid in the cure of (or at least alleviate the symptoms of) a pathological condition.

The term "pharmaceutically acceptable" has its usual meaning in the art, i.e. it is used for a substance that can be accepted as part of a medicament for human use when treating the disease in question and thus the term effectively excludes the use of highly toxic substances that would worsen rather than improve the treated subject's condition.

A "T helper lymphocyte epitope" (a $T_H$ epitope) is peptide, which binds an MHC Class II molecule and can be presented on the surface of an antigen presenting cell (APC) bound to the MHC Class II molecule. An "immunological carrier" is generally a substance of matter which includes one or many $T_H$ epitopes, and which increase the immune response against an antigen to which it is coupled by ensuring that T-helper lymphocytes are activated and proliferate. Examples of known immunological carriers are the tetanus and diphtheria toxoids and keyhole limpet hemocyanin (KLH).

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

Specific Embodiments of the Invention $1^{St}$ and $4^{th}$ Aspects

The first aspect of the invention relates to method for reducing and/or delaying pathological effects of human immunodeficiency virus I (HIV) in a human infected with HIV, the method comprising administering an effective amount of an agent capable stabilising association of the C5 domain of HIV gp120 with the transmembrane domain of gp41 and/or with the constant C2 domain of gp120. The $4^{th}$ aspect is much similar, but relates to a method of reducing the risk of developing acquired immunodeficiency syndrome (AIDS), the method comprising administering an effective amount of an agent capable of stabilising association of the C5 domain of HIV gp120 with the transmembrane domain of gp41 and/or with the constant C2 domain of gp120.

These aspects primarily aim at treating HIV infected individuals with agents which can mimic the antibodies which according to the present invention are characteristic for HIV infected long-term non-progressors—this is the most straightforward therapeutic utilisation of the findings underlying the present invention. Where the $1^{st}$ aspects aims at reducing pathological effects of HIV or prolonging the time it takes to develop manifest AIDS, the $4^{th}$ aspect aims at reducing the risk of developing AIDS altogether and may therefore be used in individuals which are currently treated prophylactically with antiretroviral therapy.

In one embodiment, the agent in the first aspect of the invention is a molecule comprising at least one amino acid sequence selected independently from an amino acid sequence derived from the transmembrane domain of gp41 and an amino acid sequence derived from the C2 domain, wherein the at least one amino acid sequence binds the C5 domain and comprises at least one D-amino acid; in certain embodiments all the amino acids in the amino acid sequence are D-amino acids. The molecule is preferably a peptide, and in certain embodiments this peptide consists of the at least one amino acid sequence. The amino acid sequences typically include at most 10 amino acid residues, such as at most 9, at most 8, at most 7, at most 6, and at most 5 amino acid residues. Preferred molecules are therefore peptides having 4, 5, 6, 7, 8, 9, or 10 amino acid residues. Specific embodiments of the at least one molecule are therefore the peptides having or comprising SEQ ID NO: 34, 35, 36, 37, 39, 40, 42, 43 and 45, which may all be composed partly or entirely of D-amino acids. Also molecules comprising peptides having Formula III are interesting embodiments of the at least one molecule.

In one embodiment, the agent in the first aspect of the invention is selected from an antibody, an antibody fragment or an antibody analogue. The antibody may be a fully human antibody, a humanized antibody, or a chimeric antibody, or a derivative thereof. Typically, the antibody is an IgA, an IgD, an IgG, an IgE or an IgM—the antibody may be both monoclonal and polyclonal. The antibody fragment is typically selected from a Fab fragment, a Fab' fragment, a Fab'-SH fragment, a F(ab)2 fragment, a F(ab')2 fragment, an Fv fragment, a Heavy chain Ig (a llama or camel Ig), a $V_{HH}$ fragment, a single domain FV, and a single-chain antibody fragment, and the antibody analogue is typically selected from a scFV, a dsFV, a minibody, a diabody, a triabody, a kappa body, an IgNAR, a tandAb, a BITE, and a multispecific antibody.

In one embodiment of the first aspect of the invention, the agent binds to and stabilises association between one or more amino acid residues in the amino acid stretch $TZ^1AKRRVVZ^2REKR$, where $Z^1$ is K, R or E and where $Z^2$ is Q or E, and one or more amino acid residues in an amino acid stretch in the transmembrane domain of gp41 and/or in the constant C2 domain of gp120. This amino acid stretch from C5 is highly conserved across the multiple HIV clades known and effective interaction with this stretch by the agent is therefore believed to be highly advantageous.

$2^{nd}$ and $3^{rd}$ Aspects

The $2^{nd}$ aspect of the invention relates to a method for reducing the risk of or reducing and/or delaying pathological effects of human immunodeficiency virus I (HIV) in a human infected with HIV, the method comprising administering an effective amount of an immunogen, which induces antibodies that stabilise association of the C5 domain of HIV gp120 with the transmembrane domain of gp41 and/or with the constant C2 domain of gp120, whereas the $3^{rd}$ aspect relates to a prophylactic method using the same means. In other words, the $2^{nd}$ aspect relates to therapeutic active immunotherapy, whereas the $3^{rd}$ aspect relates to prophylactic immunotherapy of HIV disease, including AIDS. This also entails prophylaxis of HIV infection.

These particular aspects are based on the realisation that it is feasible to induce the same type of antibody repertoire in the average HIV infected individual as the one that is found in the HIV LTNP individuals. By carefully selecting peptide regions in both C5 and in tm-gp41 and/or C2 in order to prepare peptide combinations that mimic the antibody binding epitopes present in HIV composed of these regions, it becomes possible to prepare vaccines which will induce the desired immunity—interestingly, this approach does not aim at vaccinating so as to obtain neutralizing antibodies in the classical sense.

In one embodiment the immunogen is selected from a peptide combination detailed below when discussing the fifth aspect of the invention, a composition detailed below under the sixth aspect, a nucleic acid fragment discussed in relation to the seventh aspect, a virus or plasmid vector discussed as the eighth aspect, or a plasmid or virus composition discussed under the ninth aspect.

In common for aspects 1-4 is that they all include embodiments where the targeted association between the C5 domain and C2 and/or the transmembrane domain of gp41 involves at least one amino acid in the sequence $TZ^1AKRRVVZ^2REKR$, where $Z^1$ is K, R or E and where $Z^2$ is Q or E and an amino acid and involves at least one amino acid in the transmembrane domain of gp41 or at least one amino acid in the constant C2 domain of gp120. As explained above, this particular sequence is extremely well-conserved across known HIV clades, and therefore it is the interaction between this sequence and tm-gp41 or C2 it is most feasible to target.

5$^{th}$ Aspect

The 5$^{th}$ aspect relates to a peptide combination, said combination comprising
  a first peptide comprising the amino acid sequence of the 13 amino acid residue amino acid sequence of the C5 domain of HIV gp120 including between 0 and 4 amino acid substitutions, a subsequence thereof, or an amino acid sequence comprising the inverso-, retro- or retro-inverso form of said amino acid sequence or subsequence, and
  at least one second peptide comprising an amino acid stretch present in the transmembrane domain of gp41 or present in the constant C2 domain of gp120 or comprising an amino acid stretch present in any one of SEQ ID NOs. 6-13 or comprising an inverso-, retro- or retro-inverso form of an amino acid stretch present in the transmembrane domain of gp41 or present in the constant C2 domain of gp120,
wherein said peptide combination is capable of inducing an antibody which can bind and stabilise the association of the C5 domain of HIV gp120 with the transmembrane domain of gp41 and/or with the constant C2 domain of gp120, and wherein said peptide combination lacks amino acids N-terminal of C5 in gp120.

In other words, the 5$^{th}$ aspect relates to peptide combinations which have a resemblance in 3 dimensions with the epitopes which characterise the interacting areas in C5 on the one hand and tm-gp41 and/or C2 on the other. These peptide combinations are according to the invention useful immunogens that can induce antibodies having the same characteristics as the antibodies found in HIV LTNP individuals, but the peptide combinations also are promissing as diagnostic/prognostic tools. The inclusion of retro-, inverso-, and retro-inverso peptides i.a. enables production of proteolytically stable peptides as well as peptides are truly foreign compared to the HIV counterpart.

In one embodiment of the peptide combination, said first peptide comprises the amino acid sequence having formula I:

$$X^1\text{-}X^2\text{-}X^3\text{-}X^4\text{-}X^5\text{-}X^6\text{-}X^7\text{-}X^8\text{-}X^9\text{-}X^{10}\text{-}X^{11}\text{-}X^{12}\text{-}X^{13} \quad (I)$$

wherein $X^1$ is Thr, $X^2$ is selected from Lys, Arg, Har and Glu, $X^3$ is selected from Ala and Val, $X^4$ is selected from Arg, Har, Lys and Cit (citrulline), $X^5$ is selected from Arg, Har, Lys and Cit, $X^6$ is selected from Arg, Har, Lys and Cit, $X^7$ is selected from Val, Leu, Ile and Nle (norleucin), $X^8$ is selected from Val, Leu Ile and Nle, $X^9$ is selected from Gln, Glu, Asn and Asp, $X^{10}$ is selected from Arg, Har and Cit, $X^{11}$ is selected from Glu and Asp, $X^{12}$ is Lys, and $X^{13}$ is selected from Arg, Har and Cit,
or comprises a subsequence the amino acid sequence of formula I, or comprising the inverso-, retro- or retro-inverso form of said amino acid sequence or subsequence. The first peptide may further comprise the dipeptide Ala-Pro linked to the N-terminus of the amino acid sequence having formula I and/or the first peptide may further comprise the dipeptide $X^{14}$-$X^{15}$ linked to the C-terminus of the amino acid sequence having formula I, wherein $X^{14}$ is selected from Ala and Val, and wherein $X^{15}$ is selected from Val, Leu and Nle.

Particularly interesting peptides derived from C5 are set forth in the preamble to the Examples and constitute embodiments of a first peptide of the peptide combinations of the invention.

A number of naturally occurring mutants of gp41 and gp120 has been observed, so when stating that the second peptide comprises an amino acid stretch present in the transmembrane domain of gp41 or present in the constant C2 domain of gp120, this is intended to denote that the amino acid stretch is present in any such naturally occurring form. So, the at least second peptide, when derived from gp41, is in certain embodiments one which includes the amino acid sequence having the formula:

$$Z^1\text{-}Z^2\text{-}Z^3\text{-}Z^4\text{-}Z^5\text{-}Z^6\text{-}Z^7\text{-}Z^8\text{-}Z^9\text{-}Z^{10}\text{-}Z^{11}\text{-}Z^{12}\text{-}Z^{13}\text{-}Z^{14}\text{-}Z^{15}\text{-}Z^{16}\text{—}Z^{17} \quad (III)$$

wherein $Z^1$ is Asp, $Z^2$ is Arg, $Z^3$ is Pro, $Z^4$ is Glu or Gly, $Z^5$ is Gly or Arg, $Z^6$ is Ile, $Z^7$ is Glu, $Z^8$ is Glu, $Z^9$ is Glu, $Z^{10}$ is Gly, $Z^{11}$ is Gly, $Z^{12}$ is Glu or is absent, $Z^{13}$ is Arg or Gln, $Z^{14}$ is Asp or Gly, $Z^{15}$ is Arg or Lys, $Z^{16}$ is Asp or Gly and $Z^{17}$ is Arg,
or includes a subsequence of formula (III), such as a subsequence having at least 5 amino acid residues (such as at least 6, at least 7, at least 8, at least 9, at least 10, at least 11, at least 12, at least 13, at least 14, at least 15, and at least 16 amino acid residues). Further, this embodiment of the second peptide may contain amino acid substitutions which result in a sequence identity of at least 80% with a corresponding amino acid sequence found in gp41.

Particularly interesting peptides derived from C20 and gp41 are set forth in the preamble to the Examples and constitute embodiments of a second peptide of the peptide combinations of the invention.

In certain embodiments of the peptide combination, the first peptide and the at least one second peptide are associated via a linker; the linker can be any peptide linker, such as a glycine, a lysine or an arginine linker, a polyhistidinyl tag, Protein G, and Protein A but it is also possible to use a bis-maleimide linker, a disulfide linker, or a polyethylene glycol (PEG) linker. In practice, any linker found useful in peptide chemistry is also useful as a linker according to the present invention. Thus, the invention contemplates the use of "simple" linear peptides which are conjugated or fused to each other, but also peptide combinations where the individual peptides derived from C5 and other regions of gp120 or gp41 are linked via non-peptide linkers e.g. complementary nucleic acids, nucleic acid derivatives or analogues e.g. PNA, LNA. Use of multiple linker types are also within the scope of the present invention, and it is e.g. also a part of the invention to utilise linear peptides which include intrachain disulphide linkers.

Particularly interesting peptide combinations of the invention are set forth in the preamble to the examples.

In certain embodiments, at least one of the first and at least one second peptides in the peptide combination comprises an N- or C-terminal modification, such as an amidation, acylation, or acetylation.

Since the peptide combinations are contemplated as vaccine agents or diagnostic agents, they are in certain embodiments coupled to a carrier molecule, such as an immunogenic carrier. The peptides of the peptide combinations may thus be linked to other molecules either as recombinant fusions (e.g. via CLIP technology) or through chemical linkages in an oriented (e.g. using heterobifunctional cross-linkers) or nonoriented fashion. Linking to carrier molecules such as for example diphtheria toxin, latex beads (convenient in diagnostic and prognostic embodiments), and magnetic beads (also convenient in diagnostic and prognostic embodiments), polylysine constructs etc, are all possible according to the invention.

The immunogenic carrier is conveniently selected from carrier proteins such as those conventionally used in the art (e.g. diphtheria or tetanus toxoid, KLH etc.), but it is also possible to use shorter peptides (T-helper epitopes) which can induce T-cell immunity in larger proportions of a population. Details about such T-helper epitopes can e.g. be found in WO 00/20027, which is hereby incorporated by reference herein—all immunologic carriers and "promiscuous" (i.e. universal) T-helper epitopes discussed therein are useful as immunogenic carriers in the present invention.

In certain embodiments, the carrier is a virus like particle, i.e. a particle sharing properties with virions without being infectious. Such virus-like particles may be provided chemically (e.g. Jennings and Bachmann Ann Rev Pharmacol. Toxicol. 2009. 49:303-26 Immunodrugs: Therapeutic VLP-based vaccines for chronic diseases) or using cloning techniques to generate fusion proteins (e.g. Peabody et al. J. Mol. Biol. 2008; 380: 252-63. Immunogenic display of diverse peptides on virus-like particles of RNA phage MS2). Another example is "Remune", an HIV vaccine originally made by Immune Response Corporation, which consists of formalin inactivated HIV that has been irradiated to destroy the viral genome. The company was started by Jonas Salk who used the same technique to generate the killed polio vaccine in widespread use today. However, on fixation of HIV, gp120 fell off leaving only gp41 on the virion surface. This opens for the possibility of directly admixing C5-derived peptides disclosed herein with Remune particles, because it should still be possible to obtain the binding between C5 and gp41 on a Remune particle.

Embodiments of the fifth aspect also include those wherein the first peptide is selected from the group consisting of SEQ ID NO: 1, 2, 3, 4, and 5 or a fragment thereof, or the inverso-, retro- or retro-inverso form of a peptides selected from SEQ ID NO: 1, 2, 3, 4, and 5 or a fragment thereof, and wherein the second peptide is selected from the group consisting of SEQ ID NO: 6, 7, 8, 9, 10, 11, 12, 13, or 46 or a fragment thereof or the inverso-, retro- or retro-inverso form of a peptides selected from SEQ ID NO: 6, 7, 8, 9, 10, 11, 12, 13, or 46 or a fragment thereof. As mentioned above, in such a case the fragment may be very short, as long as the peptide combination provides for the ability to induce antibodies which will stabilise association between C5 and gp41 and/or C2. A number of interesting peptide combinations of the present invention are listed in the Preamble to the Examples.

In an embodiment, the peptide combination of the invention comprises at most 70 amino acids, such as the most 69, at most 68, at most 67, at most 66, at most 65, at most 64, at most 63, at most 62, at most 61, at most 60, at most 59, at most 58, at most 57, at most 56, at most 55, at most 54, at most 53, at most 52, at most 51, at most 50, at most 49, at most 48, at most 47, at most 46, at most 45, at most 44, at most 43, at most 42, at most 41, at most 40, at most 39, at most 38, at most 37, at most 36, at most 35, at most 34, at most 33, at most 32, at most 31, at most 30, at most 29, at most 28, at most 27, at most 26, at most 25, at most 24, at most 23, at most 22, at most 21, at most 20, at most 19, at most 18, at most 17, at most 16, at most 15, at most 14, at most 13, at most 12, at most 11, at most 10, at most 9, at most 8, and at most 7 amino acids.

In an embodiment, the peptide combination of the invention comprises at least 6 amino acid residues, such as at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, and at least 69 amino acid residues.

In one embodiment, the peptide combination of the invention consists of 6 amino acid residues or 7 amino acid residues or 8 amino acid residues or 9 amino acid residues or 10 amino acid residues or 11 amino acid residues or 12 amino acid residues or 13 amino acid residues or 14 amino acid residues or 15 amino acid residues or 16 amino acid residues or 17 amino acid residues or 18 amino acid residues or 19 amino acid residues or 20 amino acid residues or 21 amino acid residues or 22 amino acid residues or 23 amino acid residues or 24 amino acid residues or 25 amino acid residues or 26 amino acid residues or 27 amino acid residues or 28 amino acid residues or 29 amino acid residues or 30 amino acid residues or 31 amino acid residues or 32 amino acid residues or 33 amino acid residues or 34 amino acid residues or 35 amino acid residues or 36 amino acid residues or 37 amino acid residues or 38 amino acid residues or 39 amino acid residues or 40 amino acid residues or 41 amino acid residues or 42 amino acid residues or 43 amino acid residues or 44 amino acid residues or 45 amino acid residues or 46 amino acid residues or 47 amino acid residues or 48 amino acid residues or 49 amino acid residues or 50 amino acid residues or 51 amino acid residues or 52 amino acid residues or 53 amino acid residues or 54 amino acid residues or 55 amino acid residues or 56 amino acid residues or 57 amino acid residues or 58 amino acid residues or 59 amino acid residues or 60 amino acid residues or 61 amino acid residues or 62 amino acid residues or 63 amino acid residues or 64 amino acid residues or 65 amino acid residues or 66 amino acid residues or 67 amino acid residues or 68 amino acid residues or 69 amino acid residues or 70 amino acid residues.

$6^{th}$ Aspect of the Invention

This aspect relates to an immunogenic composition (such as a vaccine composition) comprising a peptide combination described under the $5^{th}$ aspect in combination with a pharmaceutically acceptable diluent or vehicle and optionally an immunological adjuvant.

Preparation of immunogenic compositions include the use of state-of-the-art constituents such as immunological adjuvants. Apart from these adjuvants, which are detailed below, immunogenic compositions are prepared as generally taught in the art:

Preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines; cf. the detailed discussion of adjuvants below.

The vaccines are conventionally administered parenterally, by injection, for example, either subcutaneously, intracutaneously, intradermally, subdermally or intramuscularly. Additional formulations which are suitable for other modes of administration include suppositories and, in some cases, oral, buccal, sublingual, intraperitoneal, intravaginal, anal, epidural, spinal, and intracranial formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10-95% of active ingredient, preferably 25-70%.

The peptides and peptide combinations may be formulated into the vaccine as neutral or salt forms. Pharmaceutically acceptable salts include acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of immunity desired. Suitable dosage ranges are of the order of several hundred micrograms active ingredient per vaccination with a preferred range from about 0.1 µg to 2,000 µg (even though higher amounts in the 1-10 mg range are contemplated), such as in the range from about 0.5 µg to 1,000 µg, preferably in the range from 1 µg to 500 µg and especially in the range from about 10 µg to 100 µg. Suitable regimens for initial administration and booster shots are also variable but are typified by an initial administration followed by subsequent inoculations or other administrations.

Some of the peptides and peptide combinations are sufficiently immunogenic in a vaccine, but for some of the others the immune response will be enhanced if the vaccine further comprises an adjuvant substance. The immunogenic molecules described herein can be therefore be formulated with adjuvants:

The adjuvants—to be combined are known to induce humoral responses and include: i) Salt suspensions (e.g. varieties of salts containing aluminum ions or calcium ions), ii) Oil-in-water emulsions (e.g. varieties of squalane-based or squalene-based emulsions), iii) Water-in-oil emulsions (e.g. Montanide ISA51 or ISA720), iv) Neutral liposomes, v) Cationic liposomes, vi) Microspheres, vii) Immunostimulating complexes (e.g. ISCOMs or ISCOMATRIX), viii) Pattern-recognition receptor agonists (e.g. agonists for C-type lectin receptors (CLRs), NOD-like receptors (NLRs), RIG-like helicases (RLHs), Triggering receptor expressed on myeloid cells (TREMs) and Toll-like receptors (TLRs)), ix) Saponins (i.e. Any saponin derived from Quillaja *saponaria* or Platycodon *grandiflorum*), x) Virosomes/Virus-like particles (e.g.), xi) Enterotoxins (i.e. Cholera toxin, CTA1-DD or *Esherichia coli* heat-labile enterotoxin), and combinations thereof.

Various methods of achieving adjuvant effect for the vaccine are thus known. General principles and methods are detailed in "The Theory and Practical Application of Adjuvants", 1995, Duncan E. S. Stewart-Tull (ed.), John Wiley & Sons Ltd, ISBN 0-471-95170-6, and also in "Vaccines: New Generationn Immunological Adjuvants", 1995, Gregoriadis G et al. (eds.), Plenum Press, New York, ISBN 0-306-45283-9, both of which are hereby incorporated by reference herein, but a number of later publications also deal with the technology of incorporating adjuvants: Roestenberg M et al., PLoS One. 2008; 3(12):e3960. Epub 2008 Dec. 18; Relyveld E and Chermann J C, Biomed Pharmacother. 1994; 48(2):79-83; Hsu F J et al., Blood. 1997 May 1; 89(9):3129-35; Galli G et al., Proc Natl Acad Sci USA. 2009 May 12; 106(19):7962-7. Epub 2009 Apr. 27; Bojang K A et al., Lancet. 2001 Dec. 8; 358(9297):1927-34; Odunsi K et al., Proc Natl Acad Sci USA. 2007 Jul. 31; 104(31):12837-42. Epub 2007 Jul. 25; Patel G B and Sprott G D; Crit Rev Biotechnol. 1999; 19(4): 317-57. Review; Agger E M et al., PLoS One. 2008 Sep. 8; 3(9):e3116; Kirby D J et al. J Drug Target. 2008 May; 16(4): 282-93; Florindo H F et al., Vaccine. 2008 Aug. 5; 26(33):4168-77. Epub 2008 Jun. 17; Sun H X et al., Vaccine. 2009 May 28; Guy B, Nat Rev Microbiol. 2007 July; 5(7):505-17. Review; Vandepapelière P et al., Vaccine. 2008 Mar. 4; 26(10):1375-86. Epub 2008 Jan. 14; Ghochikyan A et al. Vaccine. 2006 Mar. 20; 24(13): 2275-82. Epub 2005 Dec. 5; Xie Y et al., Vaccine. 2008 Jun. 25; 26(27-28):3452-60. Epub 2008 May 1; Chung Y C et al., Vaccine. 2008 Mar. 28; 26(15):1855-62. Epub 2008 Feb. 25; Maier M et al., Vaccine. 2005 Oct. 25; 23(44): 5149-59; Sundling C et al., J Gen Virol. 2008 December; 89(Pt 12):2954-64.

7$^{th}$ Aspect of the Invention

This aspect relates to a nucleic acid fragment encoding a subset of peptide combinations of the invention, namely those which can be expressed as one single expression product or 2 or more expression products (which can associate) by a pro- or eukaryotic cell. Thus, according to this aspect is provided a nucleic acid fragment encoding a peptide combination, said peptide combination comprising a first peptide as detailed above with the proviso that the amino acid residues in said first peptide are L-forms selected from the group consisting of Ala, Cys, Asp, Glu, Phe, Gly, His, Ile, Lys, Leu, Met, Asn, Pro, Gln, Arg, Ser, Thr, Val, Trp, and Tyr, and at least one second peptide as discussed above, with the proviso that the amino acid residues in said second peptide are L-forms, wherein said peptide combination is capable of inducing an antibody which can bind and stabilise the association of the C5 domain of HIV gp120 with the transmembrane domain of gp41 and/or with the constant C2 domain of gp120, and wherein said peptide combination lacks amino acids N-terminal of C5 in gp120.

In an embodiment, this nucleic acid fragment is one, where the encoded first peptide and the encoded at least one second peptide are associated via a peptide linker and/or a disulphide bridge. The peptide linker is typically selected from the group consisting of a glycine linker, a lysine linker, a glycine-lysine linker and an Arg linker, but any peptide linker known in the art may be useful. The term peptide linker thus also is intended to denote coupling between the first and second peptide via a peptide bond. Also, the first and second peptides may be linked via a peptide linker and a disulphide bond, as is the case when an intrachain disulphide bond is established.

In one embodiment, the nucleic acid fragment encodes the peptide combination, which is coupled (by fusion) to a carrier molecule, such as an immunogenic carrier; useful carriers are discussed above.

In one embodiment, the nucleic acid fragment of the invention encodes the peptide, which is selected from the group consisting of SEQ ID NO: 1, 2, 3, 4, 5, 28, 30, 38, 41, and 44, or a fragment thereof, and encodes the second peptide selected from the group consisting of SEQ ID NO: 6, 7, 8, 9, 10, 11, 12, 13, 29, 31, 33, 37, 39, 40, 42, 43, 45, and 46 or a fragment thereof.

In an embodiment, the nucleic acid fragment encodes a peptide combination, which comprises at most 70 amino acids. In an embodiment the nucleic acid fragment encodes a peptide combination, which comprises at least 6 amino acid residues. In yet another embodiment the nucleic acid fragment of the invention encodes a peptide combination, which consist of a number of amino acid residues selected from the group consisting of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, and 70 amino acid residues amino.

$8^{th}$ Aspect

The invention also relates to a vector comprising the nucleic acid fragment according to the $7^{th}$ aspect of the invention. The term vector is in this context understood as an agent, which is capable of carrying genetic information and can deliver this genetic information into a cell. Typical vectors are selected from the group consisting of a plasmid, a virus, a phage, a cosmid, and a minichromosome.

Vectors can be in the form of cloning vectors (i.e. vectors used for transferring genetic information into cells which may be propagated and selected for the presence or absence of the genetic information), and expression vectors (i.e. vectors which include the necessary genetic elements to allow expression of genetic information of the vector in a cell). Hence, cloning vectors will typically include a selection marker as well as an origin of replication matching the cell type for which the cloning vector is intended, whereas expression vectors include regulatory elements necessary to effect expression in the intended target cell.

The nucleic acid fragments of the invention will thus normally be inserted in suitable vectors to form cloning or expression vectors carrying the nucleic acid fragments of the invention; such novel vectors are also part of the invention. Details concerning the construction of these vectors of the invention will be discussed in context of transformed cells and microorganisms below. The vectors can, depending on purpose and type of application, be in the form of plasmids, phages, cosmids, mini-chromosomes, or virus, but also naked DNA which is only expressed transiently in certain cells is an important vector. Preferred cloning and expression vectors of the invention are capable of autonomous replication, thereby enabling high copy-numbers for the purposes of high-level expression or high-level replication for subsequent cloning.

The general outline of an expression vector of the invention comprises the following features in the 5'->3' direction and in operable linkage: a promoter for driving expression of the nucleic acid fragment of the invention, optionally a nucleic acid sequence encoding a signal peptide enabling secretion (to the extracellular phase or, where applicable, into the periplasma) of or integration into the membrane of the peptide expression product, the nucleic acid fragment of the invention, and optionally a nucleic acid sequence encoding a terminator. When operating with expression vectors in producer strains or cell-lines it is for the purposes of genetic stability of the transformed cell preferred that the vector when introduced into a host cell is integrated in the host cell genome. In contrast, when working with vectors to be used for effecting in vivo expression in an animal (i.e. when using the vector in DNA vaccination) it is for security reasons preferred that the vector is incapable of being integrated in the host cell genome; typically, naked DNA or non-integrating viral vectors are used, the choices of which are well-known to the person skilled in the art The expression vectors of the invention are used to transform host cells to produce the peptide combinations of the invention. Such transformed cells, which are also part of the invention, can be cultured cells or cell lines used for propagation of the nucleic acid fragments and vectors of the invention, or used for recombinant production of the peptide combinations of the invention. Alternatively, the transformed cells can be suitable live vaccine strains wherein the nucleic acid fragment (one single or multiple copies) have been inserted so as to effect secretion or integration into the bacterial membrane or cell-wall of the peptide combination.

Preferred transformed cells of the invention are microorganisms such as bacteria (such as the species *Escherichia* [e.g. *E. coli*], *Bacillus* [e.g. *Bacillus subtilis*], *Salmonella*, or *Mycobacterium* [preferably non-pathogenic, e.g. *M. bovis* BCG]), yeasts (such as *Saccharomyces cerevisiae*), and protozoans. Alternatively, the transformed cells are derived from a multicellular organism such as a fungus, an insect cell, a plant cell, or a mammalian cell. Most preferred are cells derived from a human being, cf. the discussion of cell lines and vectors below.

For the purposes of cloning and/or optimized expression it is preferred that the transformed cell is capable of replicating the nucleic acid fragment of the invention. Cells expressing the nucleic fragment are preferred useful embodiments of the invention; they can be used for small-scale or large-scale preparation of the peptide combinations of the invention or, in the case of non-pathogenic bacteria, as vaccine constituents in a live vaccine.

When recombinantly producing the peptide combinations of the invention by means of transformed cells, it is convenient, although far from essential, that the expression product is either exported out into the culture medium or carried on the surface of the transformed cell.

When an effective producer cell has been identified it is preferred, on the basis thereof, to establish a stable cell line which carries the vector of the invention and which expresses the nucleic acid fragment of the invention. Preferably, this stable cell line secretes or carries the peptide expression product, thereby facilitating purification thereof.

In general, plasmid vectors containing replicon and control sequences which are derived from species compatible with the host cell are used in connection with the hosts. The vector ordinarily carries a replication site, as well as marking sequences which are capable of providing phenotypic selection in transformed cells. For example, *E. coli* is typically transformed using pBR322, a plasmid derived from an *E. coli* species (see, e.g., Bolivar et al., 1977). The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the prokaryotic microorganism for expression.

Those promoters most commonly used in recombinant DNA construction include the β-lactamase (penicillinase) and lactose promoter systems (Chang et al., 1978; Itakura et al., 1977; Goeddel et al., 1979) and a tryptophan (trp) promoter system (Goeddel et al., 1979; EP-A-0 036 776). While these are the most commonly used, other microbial promoters have been discovered and utilized, and details concerning their nucleotide sequences have been published.

In addition to prokaryotes, eukaryotic microbes, such as yeast cultures may also be used, and also here the promoter should be capable of driving expression. *Saccharomyces cerevisiase*, or common baker's yeast is the most commonly used among eukaryotic microorganisms, although a number of other strains are commonly available. For expression in *Saccharomyces*, the plasmid YRp7, for example, is commonly used (Stinchcomb et al., 1979; Kingsman et al., 1979; Tschemper et al., 1980).

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also incorporated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. Examples of such useful host cell lines are VERO and HeLa cells, Chinese hamster ovary (CHO) cell lines, and W138, BHK, COS-7 293, *Spodoptera frugiperda* (SF) cells, *Drosophila melanogaster* cell lines (such as Schneider 2 ($S_2$)), and MDCK cell lines.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., other Polyoma viruses, Adeno, VSV, BPV) or may be provided by the host cell chromosomal replication mechanism. If the vector is integrated into the host cell chromosome, the latter is often sufficient.

$9^{th}$ Aspect

As discussed above, the nucleic acid fragment or vector of the invention may in its own right be suitable as a immunizing agent (e.g. a vaccine agent), i.e. in the form of an immunogenic composition comprising a nucleic acid fragment or a vector of the present invention in combination with a pharmaceutically acceptable diluent or vehicle and optionally an immunological adjuvant.

As an alternative to classic administration of a peptide-based vaccine, the technology of nucleic acid vaccination (also known as "nucleic acid immunisation", "genetic immunisation", and "gene immunisation") offers a number of attractive features.

First, in contrast to the traditional vaccine approach, nucleic acid vaccination does not require resource consuming large-scale production of the immunogenic agent (e.g. in the form of industrial scale fermentation of microorganisms or large scale peptide synthesis). Furthermore, there is no need to device purification and refolding schemes for the immunogen. And finally, since nucleic acid vaccination relies on the biochemical apparatus of the vaccinated individual in order to produce the expression product of the nucleic acid introduced, the optimum post-translational processing of the expression product is expected to occur.

In this embodiment, the introduced nucleic acid is preferably DNA which can be in the form of naked DNA, DNA formulated with charged or uncharged lipids, DNA formulated in liposomes, DNA included in a viral vector, DNA formulated with a transfection-facilitating protein or polypeptide, DNA formulated with a targeting protein or polypeptide, DNA formulated with Calcium precipitating agents, DNA coupled to an inert carrier molecule, DNA encapsulated in a polymer, e.g. in PLGA (cf. the microencapsulation technology described in WO 98/31398) or in chitin or chitosan, and DNA formulated with an adjuvant. In this context it is noted that practically all considerations pertaining to the use of adjuvants in traditional vaccine formulation apply for the formulation of DNA vaccines. Hence, all disclosures herein which relate to use of adjuvants in the context of polypeptide based vaccines apply *mutatis mutandis* to their use in nucleic acid vaccination technology.

As for routes of administration and administration schemes of polypeptide based vaccines which have been detailed above, these are also applicable for the nucleic acid vaccines of the invention and all discussions above pertaining to routes of administration and administration schemes for polypeptides apply *mutatis mutandis* to nucleic acids. To this should be added that nucleic acid vaccines can also be administered intraveneously and intraarterially. Furthermore, it is well-known in the art that nucleic acid vaccines can be administered by use of a so-called gene gun and/or by use of electroporation, and hence also these and equivalent modes of administration are regarded as part of the present invention.

Under normal circumstances, the nucleic acid fragment is introduced in the form of a vector wherein expression is under control of a viral promoter. For more detailed discussions of vectors according to the invention, cf. the discussion above. Also, detailed disclosures relating to the formulation and use of nucleic acid vaccines are available, cf. Donnelly J J et al, 1997, Annu. Rev. Immunol. 15: 617-648 and Donnelly J J et al., 1997, Life Sciences 60: 163-172. Both of these references are incorporated by reference herein.

An alternative of using peptide immunogens or nucleic acid immunogens is the use of live immunogen technology. This entails administering a non-pathogenic microorganism which has been transformed with a nucleic acid fragment or a vector of the present invention. The non-pathogenic microorganism can be any suitable attenuated bacterial strain (attenuated by means of passaging or by means of removal of pathogenic expression products by recombinant DNA technology), e.g. *Mycobacterium bovis* BCG., non-pathogenic *Streptococcus* spp., *E. coli, Salmonella* spp., *Vibrio cholerae*, Shigella, etc. Reviews dealing with preparation of state-of-the-art live vaccines can e.g. be found in Saliou P, 1995, Rev. Prat. 45: 1492-1496 and Walker P D, 1992, Vaccine 10: 977-990, both incorporated by reference herein. For details about the nucleic acid fragments and vectors used in such live vaccines, cf. the discussion below.

As an alternative to bacterial live immunogens, the nucleic acid fragment of the invention can be incorporated in a non-virulent viral vaccine vector such as a vaccinia strain or any other suitable poxvirus.

Normally, the non-pathogenic microorganism or virus is administered only once to a subject, but in certain cases it may be necessary to administer the microorganism/virus more than once in a lifetime in order to maintain protective immunity. It is even contemplated that immunization schemes as those detailed above for polypeptide vaccination will be useful when using live or virus vaccines.

Alternatively, live or virus immunization is combined with previous or subsequent polypeptide and/or nucleic acid immunization. For instance, it is possible to effect primary immunization with a live or virus vaccine followed by subsequent booster immunizations using the polypeptide or nucleic acid approach.

10$^{th}$ Aspect

This aspect relates to a method for determining the presence of antibodies which bind an epitope composed of amino acids in the C5 domain of gp120 as well as of amino acids in the transmembrane domain of gp41 and/or the constant C2 domain of gp120, the method comprising contacting a sample potentially comprising said antibodies with at least one peptide combination of the present invention, and determining quantitatively or qualitatively binding between said at least one peptide combination and antibodies in said sample. The method can take any convenient form, and may e.g. be in the form of a non-competitive or competitive ELISA, RIA, or magnetic immunoassay, an agglutination assay, and a surface plasmon resonance based assay such as a Biacore assay.

This aspect has both diagnostic and prognostic value: With respect to prognosis, it becomes possible to discriminate LTNP HIV infected individuals from other HIV infected, thus providing knowlegde of the prognosis of these individuals and also providing guides for the type of treatment (if any) these individuals should be offered, i.e. a diagnostic tool. Also the method will allow monitoring of efficacy of the treatments taught herein, especially those which rely on immunization with immungenic agents which will induce the production of antibodies reactive with complexes between C5 and tm-pg 41 and/or C2.

Related to this aspect of the invention is the 11$^{th}$ aspect which relates to a kit for determining the presence of antibodies which bind an epitope composed of amino acids in the C5 domain of gp120 as well as of amino acids in the transmembrane domain of gp41 and/or the constant C2 domain of gp120, the kit comprising at least one peptide combination of the present invention, means for reacting a liquid sample with said peptide combination, and means for determining the presence of a positive or negative binding reaction between antibodies and said peptide combination.

Typical formats of such kits will include vessels for isolating and/or storing the liquid sample, vessels and reagents for contacting the peptide combination with the sample and means for establishing the presence of binding between peptide combinations and the constituents in the sample. In order to establish presence of such antibodies, the kit may for instance utilise secondary labelled anti-human antibodies, where the label may be any suitable label, such as a fluorescent or radioactive label, an enzymatic label, or a binding label (such as a biotin label for binding to strepavidin). In the kit, the peptide combinations may be bound to a solid support or at least the kit may include a solid support adapted to bind the peptide combinations.

12$^{th}$ Aspect

This aspect relates to identification and/or isolation of agents capable of stabilising association of the C5 domain of HIV gp120 with the transmembrane domain of gp41 and/or with the constant C2 domain of gp120 (i.e. identification and/or isolation of agents useful in some of the treatments taught herein), the method comprising testing candidate agents for their ability to displace a reference agent, which has previously been established to be capable of stabilising said association, from its stabilising binding to said C5 domain and to said transmembrane domain of gp41 and/or said C2 domain or from its binding to a surrogate of said C5 domain and of said transmembrane domain and/or said C2 domain, and isolating those candidate agents which are capable of displacing said reference agent, or testing candidate agents for their ability to bind to a surrogate of a complex between the C5 domain and the transmembrane domain of gp41 and/or the C2 domain of gp120 and isolating those agents which are capable of exerting significant binding to said surrogate.

The first of these alternatives may be put into practice in a format similar to a competitive ELISA, where the reference agent may or may not be an antibody and where the measured signal is displacement of this reference agent from its binding. The term "surrogate" does in this context denote a substance which has at least one epitope in common with C5 bound to tm-gp41 and/or C2, where this epitope does not appear with the same binding affinity in isolated C5, tm-gp41 or C2. So, the surrogate may e.g. be a peptide combination of the present invention.

Use of the surrogate for testing of direct binding candidate agents as in the above second alternative is also a possibility—in such a case, the surrogate should be validated with respect to its ability to compete with the C5 complexes taught herein to e.g. antibodies. One possible assay is a plasmon surface resonance based assay, which has the advantage of not requiring any labelling of test agent or reference agent. However, various chromatographic capture assays may also be used. Other assays include NMR and circular dichroism. The screening of molecules is in those cases based on demonstration of a shift in temperature required to separate C5 and gp41/C2 when combined with a small molecule, since the separation can be detected with both methods.

13th aspect

This aspect relates to novel analogues of C5 domain of gp120, comprising the amino acid sequence having formula II $$Y^1\text{-}Y^2\text{-}Y^3\text{-}Y^4\text{-}Y^5\text{-}Y^6\text{-}Y^7\text{-}Y^8\text{-}Y^9\text{-}Y^{10}\text{-}Y^{11}\text{-}Y^{12}\text{-}Y^{13} \quad (II)$$

wherein $Y^1$ is T, $Y^2$ is selected from Lys, Arg, Har and Glu, $Y^3$ is selected from Ala and Val, $Y^4$ is selected from Arg, Har, Lys and Cit (citrulline), $Y^5$ is selected from Arg, Har, Lys and Cit, $Y^6$ is selected from Arg, Har, Lys and Cit, $Y^7$ is selected from Val, Leu, Ile and Nle (norleucin), $Y^8$ is selected from Val, Leu Ile and Nle, $Y^9$ is selected from Gln, Glu, Asn and Asp, $Y^{19}$ is selected from Arg, Har and Cit, $Y^{11}$ is selected from Glu and Asp, $Y^{12}$ is Lys, and $Y^{13}$ is selected from Arg, Har and Cit, and wherein $Y^3$ is Val and/or wherein $Y^4$ is selected from Arg, Har and Cit and/or wherein $Y^5$ is selected from Lys and Cit and/or wherein $Y^6$ is selected from Lys and Cit and/or wherein $Y^2$ is selected from Leu, Ile and Nle and/or wherein $Y^8$ is selected from Leu Ile and Nle and/or wherein $Y^9$ is selected from Glu, Asn and Asp and/or wherein $Y^{19}$ is Cit or $Y^{11}$ is Asp or $Y^{13}$ is Cit or comprises a subsequence of at least 6 amino acid residues of the amino acid sequence of formula II, or comprises the inverso-, retro- or retro-inverso form of said amino acid sequence or subsequence.

It is contemplated that these analogues will be useful in the same way as the above-discussed peptide combinations, since they will be capable of inducing antibodies against C5 and the analogues are therefore useful in compositions for both pharmaceutical and diagnostic use. All disclosures above, which relate to the use and formulation of peptide combinations of the invention therefore apply *mutatis mutandis* to the analogues of this invention.

In contrast to the peptide combinations of the invention, the antibodies induced can target both regions having relevance for the dissociation of C5 from gp41 or from C2, but the antibodies can also target other regions of C5 which are directly responsible for immune activation.

Compared to the native C5 sequence, formula II has in some embodiments at most 5 amino acid substitutions, such as the most 4, at most 3, and at most 2 amino acid substitutions. In other embodiments, the sequence includes exactly 5 or exactly 4 or exactly 3 or exactly 2 or exactly 1 amino acid substitution compared to any native C5 sequence.

Combination Treatment

The presently disclosed methods for treatment or prophylaxis of AIDS may be combined with any known current treatment scheme used for HIV positive individuals. Notably, the methods may be combined with or preceded or followed by antiretroviral treatment or chemokine therapy. The presently claimed methods may replace or contribute to pre-exposure prophylaxis (PREP) for individuals at high risk for infection. Alternatively, the present methods may applied made in combination with antiretroviral therapy as post-exposure prophylaxis. The presently claimed methods may also be used in combination with Remune, cyclooxygenase inhibitors and pomalinomide and other adjuvants.

Preamble To Examples

Overview Sequences and Abbreviations
C5-sequences:

```
                                    (SEQ ID NO: 1)
APTKAKRRVVQREKRAV (SEQ ID NO: 2)
APTKAKRRVVEREKRAV (SEQ ID NO: 3)
APTRAKRRVVQREKRAV (SEQ ID NO: 4)
APTRAKRRVVEREKRAV (SEQ ID NO: 5)
APTEAKRRVVEREKRAV (SEQ ID NO: 44)
WWGCAKRRVCGGAKRRVVQREKRA
```

(underlined amino acid residues in SEQ ID NO: 44 are linked via a disulphide linker; the N-terminal W is preferably a D-amino acid and the C-terminal A may be amidated; the peptide is termed BI450-AdjBT_1, when having these two modifications).

C5-complex forming sequences:
DRPEGIEEEGGERDR (where amino acid 4 can be G and/or where amino acid 5 can be R and/or where amino acid 13 can be Q and/or where amino acid 14 can be G and/or where amino acid 15 can be K; SEQ ID NO: 6);
DRPEGIENNGGERDR (SEQ ID NO: 7 where amino acid 4 can be G and/or where amino acid 5 can be R and/or where amino acid 13 can be Q and/or where amino acid 14 can be G and/or where amino acid 15 can be K);
DRPEGIENNGGERDRDR (where amino acid 4 can be G and/or where amino acid 5 can be R and/or where amino acid 13 can be Q and/or where amino acid 14 can be G and/or where amino acid 15 can be K and/or where amino acid 16 can be G); SEQ ID NO: 46).
VERYLKDQQLLG (SEQ ID NO: 8);
VERYLKDEELLG (SEQ ID NO: 9);
VERYLKDNNLLG (SEQ ID NO: 10);
QLLLNGSLAEEEIVI (SEQ ID NO: 11, not yet synthesized)
QLLLNGSLAEEEVVIV (SEQ ID NO: 12, not yet synthesized)
QLLLNSLAEEEVVI (SEQ ID NO: 13, not yet synthesized)
GGAIVNGSLADDDIVI (SEQ ID NO: 37, also termed 204d herein)
WWGCIEEEGCGGIEEEGGERDR (SEQ ID NO: 45: underlined amino acid residues are linked via a disulphide linker; the N-terminal W is preferably a D-amino acid and the C-terminal R may be amidated; the peptide is termed BI450-AdjBT_2, when having these two modifications).
Polypeptides I:
$(Z\text{-}SEQ_{c5}\text{-}Z\text{-}SEQ_{c5})_n$
n=1,2,3,4
Polypeptides II:
$(Z\text{-}SEQ_{cx}\text{-}Z\text{-}SEQ_{cx})_n$
n=1,2,3,4
Peptide complexes:

```
(Z-SEQ_c5-Z-SEQ_c5)_n
    |
    Bis-maleimide linker
    |
(Z-SEQ_cx-Z-SEQ_cx)_n
    n = 1, 2, 3, 4
```

-continued $$(Z\text{-}SEQ_{c5}\text{-}Z\text{-}SEQ_{c5})_n$$
$$|$$
$$(Z\text{-}SEQ_{cx}\text{-}Z\text{-}SEQ_{cx})_n$$
$$n = 1, 2, 3, 4$$

Examples of polypeptides I can be, but are not restricted to, the following sequences:

```
                                          (SEQ ID NO: 14)
APTKAKRGGGAPTRAKRGGGAPTEAKR (SEQ ID NO: 15)
RVVEREKGGGAKRRVVGGGRVVQREK (SEQ ID NO: 16)
GGAKRRVVGGAKRRVVGQREKRAV (SEQ ID NO: 17)
CGGAKRRVVGGAKRRVVGQREKRAV (SEQ ID NO: 18)
GGAKRRVVGGAKRRVVGGQREKR (SEQ ID NO: 19)
CGGAKRRVVGGAKRRVVGGQREKR (SEQ ID NO: 20)
GGAKRRVVGGAKRRVV (SEQ ID NO: 21)
GCGAKRRVVGGAKRRVV
```

Examples of polypeptides II can be, but are not restricted to, the following sequences:

```
                                          (SEQ ID NO: 22)
GGGDQQLLGGAEEEIVGGIEEEGGERDRDR (SEQ ID NO: 23)
CGGGDQQLLGGAEEEIVGGIEEEGGERDRDR (SEQ ID NO: 24)
GGDQQLLGGAEEEIVGGGERDR (SEQ ID NO: 25)
CGGGDQQLLGGAEEEIVGGIEEEGG (SEQ ID NO: 26)
GGAEEEVVGGDQQLL (SEQ ID NO: 27)
CGGAEEEVVGGDQQLL
```

Examples of disulfide linked constructs can be, but are not restricted to, the following linked peptide sequences:

```
CGGAKRRVVGGAKRRVVGQREKRAV (SEQ ID NO: 28)
|
CGGGDQQLLGGAEEEIVGGIEEEGGERDRDR (SEQ ID NO: 29)

CGGAKRRVVGGAKRRVVGGQREKR (SEQ ID NO: 30)
|
CGGGDQQLLGGAEEEIVGGIEEEGG (SEQ ID NO: 31)

CGGAEEEVVGGDQQLL (SEQ ID NO: 32)
|
GCGGAKRRVVGGAKRRVV (SEQ ID NO: 33)
```

The above disulfide linked constructs may e.g. be synthesised by titration of 2-pyridinesulfenyl (SPyr)-protected cysteine-containing peptides with thiol-unprotected peptides. This has proven to be a superior procedure to selectively generate disulfide-linked peptide heterodimers preventing the formation of homodimers (Schutz A et al., Tetrahedron, Volume 56, Issue 24, 9 Jun. 2000, Pages 3889-3891). Similar constructs where SEQ ID NO: 28 is disulphide linked to SEQ ID NOs 31 or 33, or where SEQ ID NO: 30 is disulphide linked to SEQ ID NOs: 29 or 33, or where SEQ ID NO: 32 is disulphide linked to SEQ ID NOs: 29 or 31 are also within the scope of the present invention.

Examples of other linked constructs can be, but are not restricted to, the following linked peptide sequences:

```
GAKRRVVGGCGGAKRRVVQREKRAGEREKRA (SEQ ID NO: 38)
|
GKGGIEEEGGRDRDRGGEQDRDR (SEQ ID NO: 39)
```

(the peptides are linked via the underlined Cys and Lys residues; the entire construct is termed BI400-B herein).

```
GAKRRVVGGCGGAKRRVVQREKRAGEREKRA (SEQ ID NO: 38)
|
GKGGIEEEGGERDRDRGGQDRDR (SEQ ID NO: 40)
```

(the peptides are linked via the underlined Cys and Lys residues; the entire construct is termed BI400-Bu1 herein).

```
GAKRRVVGGCGGAKRRVVEREKRAGQREKRA (SEQ ID NO: 41)
|
GKGGIEEEGGQDRDRGGRDRDR (SEQ ID NO: 42)
```

(the peptides are linked via the underlined Cys and Lys residues; the entire construct is termed BI400-Bu2 herein).

```
GAKRRVVGGCGGAKRRVVEREKRAGQREKRA (SEQ ID NO: 41)
|
GKGGIEEEGGEQDRDRGGERDRD (SEQ ID NO: 43)
```

(the peptides are linked via the underlined Cys and Lys residues; the entire construct is termed BI400-Bu3 herein).

In general, the exact nature of the Cys-Lys linker is inessential, as long as the linker does not introduce undesired functionality in the linked construct. The Cys-Lys linker may be established by several generally known methods. The 2 peptides, which are to be linked are synthesized according to traditional solid-phase peptide synthesis techniques of Merrifield. As one example of establishing a suitable linker, as part of the linear synthesis, instead of the cysteine, the corresponding sulfonyl halide is prepared, which in turn can enter a substitution reaction with the primary amine on the lysine side chain; this establishes a sulphonamide bridge between the cysteine and lysine residues. Other reactions involve derivatization of one or both of the thiol and amino groups in the two residues and subsequent substitution/elimination reactions between the two molecules.

The linker used in the Cys-Lys linked constructs of the Examples have is in the form of an amide bond between (2-oxo-ethyl) derivatized cysteine in one peptide and lysine in the other peptide. These Cys-Lys linked peptides were all obtained from Bachem UK Ltd. on a commercial basis.

Similar constructs where SEQ ID NO: 38 is Cys-Lys linked to SEQ ID NOs 42 or 43, or where SEQ ID NO: 41 is Cys-Lys linked to SEQ ID NOs: 39 or 40 are also within the scope of the present invention.

Small molecule inhibitors:

DQQLL (SEQ ID NO: 34)

AKRRVV (SEQ ID NO: 35)

AEEEVV (SEQ ID NO: 36)

SEQ ID NOs 34-36 are preferably composed partly or completely of D-amino acids.

Example 1

Synthesis of Peptides Using Conventional Techniques for Linear Sequences

Preparation of APTKAKRRVVQREKR (SEQ ID NO: 47)

The peptide was synthesized in amide form, from the corresponding starting point according to the general description of F-moc synthesis (Atherton et al. 1978 J. Chem. Soc. Chem Commun 539), which is below termed "the general description of synthesis.

Purity (HPLC): more than 90%.

Mass spectral analysis: Theoretical molecular weight: 1822.2

Experimental molecular weight: 1823.0 ES+

Preparation of APTKAKR (SEQ ID NO: 52)

The peptide was synthesized in amide form, from the corresponding starting point according to the general description of synthesis.

Purity (HPLC): more than 90%.

Mass spectral analysis: Theoretical molecular weight: 769.6

Experimental molecular weight: 760.7 ES+

Preparation of APTRAKR (SEQ ID NO: 53)

The peptide was synthesized in amide form, from the corresponding starting point according to the general description of synthesis.

Purity (HPLC): more than 90%.

Mass spectral analysis: Theoretical molecular weight: 797.6

Experimental molecular weight: 797.6 ES+

Preparation of APTEAKR (SEQ ID NO: 54)

The peptide was synthesized in amide form, from the corresponding starting point according to the general description of synthesis.

Purity (HPLC): more than 90%.

Mass spectral analysis: Theoretical molecular weight: 770.9

Experimental molecular weight: 770.9 ES+

Preparation of RVVEREK (SEQ ID NO: 55)

The peptide was synthesized in amide form, from the corresponding starting point according to the general description of synthesis.

Purity (HPLC): more than 90%.

Mass spectral analysis: Theoretical molecular weight: 914.1

Experimental molecular weight: 913.9 ES+

Preparation of RVVQREK (SEQ ID NO: 56)

The peptide was synthesized in amide form, from the corresponding starting point according to the general description of synthesis.

Purity (HPLC): more than 90%.

Mass spectral analysis: Theoretical molecular weight: 913.1

Experimental molecular weight: 913.0 ES+

Preparation of AKRRVV (SEQ ID NO: 57)

The peptide was synthesized in amide form, from the corresponding starting point according to the general description of synthesis.

Purity (HPLC): more than 90%.

Mass spectral analysis: Theoretical molecular weight: 726.9

Experimental molecular weight: 726.9 ES+

Preparation of DRPEGIEEEGGERDR (SEQ ID NO: 6)

The peptide was synthesized in amide form, from the corresponding starting point according to the general description of synthesis.

Purity (HPLC): more than 90%.

Mass spectral analysis: Theoretical molecular weight: 1742.1

Experimental molecular weight: 1742.8

Preparation of VERYLKDQQLLG (SEQ ID NO: 8)

The peptide was synthesized in amide form, from the corresponding starting point according to the general description of synthesis.

Purity (HPLC): more than 90%.

Mass spectral analysis: Theoretical molecular weight: 1460.7

Experimental molecular weight: 1460.1

Preparation of VERYLKDEELLG (SEQ ID NO: 9)

The peptide was synthesized in amide form, from the corresponding starting point according to the general description of synthesis.

Purity (HPLC): more than 90%.

Mass spectral analysis: Theoretical molecular weight: 1462.6

Experimental molecular weight: 1463.0

Preparation of VERYLKDNNLLG (SEQ ID NO: 10)

The peptide was synthesized in amide form, from the corresponding starting point according to the general description of synthesis.

Purity (HPLC): more than 90%.

Mass spectral analysis: Theoretical molecular weight: 1432.6

Preparation of QLLLNGSLAEEEIVI (SEQ ID NO: 11)

The peptide was synthesized in amide form, from the corresponding starting point according to the general description of synthesis.

Purity (HPLC): more than 90%.

Mass spectral analysis: Theoretical molecular weight: 1639.9

Preparation of QLLLNGSLAEEEVVI (SEQ ID NO: 58)

The peptide was synthesized in amide form, from the corresponding starting point according to the general description of synthesis.

Purity (HPLC): more than 90%.

Mass spectral analysis: Theoretical molecular weight: 1625.9

Preparation of QLLLNSLAEEEVVI (SEQ ID NO: 13)

The peptide was synthesized in amide form, from the corresponding starting point according to the general description of synthesis.

Purity (HPLC): more than 90%.

Mass spectral analysis: Theoretical molecular weight: 1568.8

Preparation of APTKAKRGGGAPTRAKRGGGAP-TEAKR (SEQ ID NO: 14)

The peptide was synthesized in amide form, from the corresponding starting point according to the general description of synthesis.

Purity (HPLC): more than 90%.

Mass spectral analysis: Theoretical molecular weight: 2647.0

Experimental molecular weight: 2646.3 ES+

Preparation of RVVEREKGGGAKRRVVGGGRVVQREK (SEQ ID NO: 15)

The peptide was synthesized in amide form, from the corresponding starting point according to the general description of synthesis.

Purity (HPLC): more than 90%.

Mass spectral analysis: Theoretical molecular weight: 2862.3

Experimental molecular weight: 2863.3 ES+

Preparation of GGAKRRVVGGAKRRVVGQREKRAV (SEQ ID NO: 16)

The peptide was synthesized in amide form, from the corresponding starting point according to the general description of synthesis.

Purity (HPLC): more than 90%.

Mass spectral analysis: Theoretical molecular weight: 2590.1

Preparation of CGGAKRRVVGGAKRRVVGQREKRAV (SEQ ID NO: 17)

The peptide was synthesized in amide form, from the corresponding starting point according to the general description of synthesis.

Purity (HPLC): more than 90%.

Mass spectral analysis: Theoretical molecular weight: 2693.2

Preparation of GGAKRRVVGGAKRRVVGGQREKR (SEQ ID NO: 18)

The peptide was synthesized in amide form, from the corresponding starting point according to the general description of synthesis.

Purity (HPLC): more than 90%.

Mass spectral analysis: Theoretical molecular weight: 2476.9

Preparation of CGGAKRRVVGGAKRRVVGGQREKR (SEQ ID NO: 19)

The peptide was synthesized in amide form, from the corresponding starting point according to the general description of synthesis.

Purity (HPLC): more than 90%.

Mass spectral analysis: Theoretical molecular weight: 2580.0

Preparation of GGAKRRVVGGAKRRVV (SEQ ID NO: 20)

The peptide was synthesized in amide form, from the corresponding starting point according to the general description of synthesis.

Purity (HPLC): more than 90%.

Mass spectral analysis: Theoretical molecular weight: 1665.0

Preparation of GCGAKRRVVGGAKRRVV (SEQ ID NO: 21)

The peptide was synthesized in amide form, from the corresponding starting point according to the general description of synthesis.

Purity (HPLC): more than 90%.

Mass spectral analysis: Theoretical molecular weight: 1768.1

Preparation of GGGDQQLLGGAEEEIVGGIEEEGGERDRDR (SEQ ID NO: 22)

The peptide was synthesized in amide form, from the corresponding starting point according to the general description of synthesis.

Purity (HPLC): more than 90%.

Mass spectral analysis: Theoretical molecular weight: 3127.2

Preparation of CGGGDQQLLGGAEEEIVGGIEEEGGERDRDR (SEQ ID NO: 23)

The peptide was synthesized in amide form, from the corresponding starting point according to the general description of synthesis.

Purity (HPLC): more than 90%.

Mass spectral analysis: Theoretical molecular weight: 3230.4

Preparation of GGDQQLLGGAEEEIVGGGERDR (SEQ ID NO: 24)

The peptide was synthesized in amide form, from the corresponding starting point according to the general description of synthesis.

Purity (HPLC): more than 90%.

Mass spectral analysis: Theoretical molecular weight: 2242.4

Preparation of CGGGDQQLLGGAEEEIVGGIEEEGG (SEQ ID NO: 25)

The peptide was synthesized in amide form, from the corresponding starting point according to the general description of synthesis.

Purity (HPLC): more than 90%.

Mass spectral analysis: Theoretical molecular weight: 2402.5

Preparation of GGAEEEVVGGDQQLL (SEQ ID NO: 26)

The peptide was synthesized in amide form, from the corresponding starting point according to the general description of synthesis.

Purity (HPLC): more than 90%.

Mass spectral analysis: Theoretical molecular weight: 1499.6

Preparation of CGGAEEEVVGGDQQLL (SEQ ID NO: 27)

The peptide was synthesized in amide form, from the corresponding starting point according to the general description of synthesis.

Purity (HPLC): more than 90%.

Mass spectral analysis: Theoretical molecular weight: 1602.7

Example 2

Synthesis of Complexed Peptides

Preparation of

```
CGGAKRRVVGGAKRRVVGQREKRAV (SEQ ID NO: 28)
|
CGGGDQQLLGGAEEEIVGGIEEEGGERDRD (SEQ ID NO: 59)
```

Purity (HPLC): more than 90%.
Theoretical molecular weight: 5750.4

Preparation of

```
CGGAKRRVVGGAKRRVVGGQREKR (SEQ ID NO: 30)
|
CGGGDQQLLGGAEEEIVGGIEEEGG (SEQ ID NO: 31)
```

Purity (HPLC): more than 90%.
Theoretical molecular weight: 4965.6

Preparation of

```
CGGAEEEVVGGDQQLL (SEQ ID NO: 32)
|
GCGGAKRRVVGGAKRRVV (SEQ ID NO: 33)
```

Purity (HPLC): more than 90%.

Theoretical molecular weight: 3410.9
Preparation of:

GAKRRVVGGCGGAKRRVVQREKRAGEREKRA (SEQ ID NO: 38)
            |
        GKGGIEEEGGRDRDRGGEQDRDR (SEQ ID NO: 39)

Purity (HPLC): more than 94%.
Theoretical molecular weight: 5876.93

Example 3

Recognition of SEQ ID NO: 47 Alone and in Combination with SEQ ID NOs: 6, 8 and 9 by Pooled Human Sera from HIV Chronically Infected Individuals, LTNP and Non-infected Blood Donors Seroreactivity to SEQ ID NO: 47 alone or in combination with SEQ ID NOs. 6 (with the sequence DRPEGIEEEGG-ERDR), 8 and 9 was determined according to a general ELISA principle either using magnetic particles as a solid support or attachment of peptides to a 96-well tray.

Methods:

In the system described below, peptide was coated on to magnetic particles using generally accepted techniques. 300 µg was coated onto particles for all peptides with the exception of SEQ ID NO: 47 where 600 µg was used. SEQ ID NO: 47 (from C5) and SEQ ID NO: 6, 8 and 9 (from gp41) were preincubated overnight at 4 degrees C. to allow interactions to form between C5 and gp41 sequences respectively and all combined. Sera were then incubated with the peptide coated beads according to established protocols. Visualisation of antibody binding to C5 peptides was achieved using protein G that can bind immunoglobulins from different species coupled to alkaline phosphatase. The positive control was commercially available serum from a sheep immunised with the C5 derived sequence APTKAKRRVVQREKR (SEQ ID NO: 47).

Pooled sera from 25 LTNP were tested for seroreactivity to SEQ ID NO: 47 alone and SEQ ID NO: 47 when in combination with SEQ ID NOs: 6 (DRPEGIEEEGGERDR), 8 and 9 respectively and all combined. Pooled sera were also tested from 12 HIV positive, chronically infected individuals and 20 sera from blood donors. The results are shown in Table A:

TABLE A

Results of seroreactivity of pooled sera to SEQ ID NO: 47 and SEQ ID NO: 47 combined with sequences to gp41. Positivity is determined visually.

| Peptide | Blood-donors pool | HIV chronically infected pool | LTNP-pool | Pos. Control |
|---|---|---|---|---|
| APTKAKRRVVQREKR (=SEQ ID NO: 47) (600 µg/ml) | + | 2+ | 4+ | >4+ |
| APTKAKRRVVQREKE (SEQ ID NO: 47) 300 µg/ml + DRPEGIEEEGGERDR (SEQ ID NO: 6) 300 µg/ml + VERYLKDQQLLG (SEQ ID NO: 8) 300 µg/ml + | (−) | Neg | 3+ | 4+ |

TABLE A-continued

Results of seroreactivity of pooled sera to SEQ ID NO: 47 and SEQ ID NO: 47 combined with sequences to gp41. Positivity is determined visually.

| Peptide | Blood-donors pool | HIV chronically infected pool | LTNP-pool | Pos. Control |
|---|---|---|---|---|
| VERYLKDEELLG (SEQ ID NO: 9) 300 µg/ml | | | | |
| APTKAKRRVVQREKE (SEQ ID NO: 47) 300 µg/ml + DRPEGIEEEGGERDR (SEQ ID NO: 6) 300 µg/ml | + | + | 2+ | 4+ |
| APTKAKRRVVQREKE (SEQ ID NO: 47) 300 µg/ml + VERYLKDQQLLG (SEQ ID NO: 8) 300 µg/ml | (−) | Neg | 2+ | 4+ |
| APTKAKRRVVQREKE (SEQ ID NO: 47) 300 µg/ml + VERYLKDEELLG (SEQ ID NO: 9) 300 µg/ml | + | Neg | + | 4+ |

Results/Discussion points: The results in Table A show that pooled LTNP sera generally provide strong reactivity to SEQ ID NO: 47 from HIV-1 when compared to pooled sera from patients chronically infected with HIV—this has been reported previously. However, combining SEQ ID NO: 47 with other peptides derived from gp41 (e.g. all combined or only SEQ ID NO: 8) reduced the level of background observed in blood donors as well as responses in pooled sera from chronically infected individuals. The response in LTNP remains strong.

Example 4

Recognition of SEQ ID NO: 47 and SEQ ID NO: 47 in Combination with SEQ ID NO: 6 by Individual Human Sera from HIV Chronically Infected, LTNP, Blood Donors Seroreactivities of individual LTNP patient sera to SEQ ID NO: 47 (16 µg) alone and in combination with SEQ ID NO: 6 (16 µg) were determined using an ELISA plate as a solid support. Sheep anti-C5 antibodies were used as a positive control. Optical density (OD) at 280 nm was used as a read out following the enzymatic reaction from protein G coupled to alkaline phosphatase. FIG. 1 shows the proportion of LTNP patients and their OD values following subtraction of background (medium alone in the absence of peptide).

FIG. 1 shows that a greater proportion of LTNP sera (n=8, 2 most right-hand, grey bars) have reactivity to SEQ ID NO: 47 when it is in combination (i.e. >80% ratio) with SEQ ID NO: 6 (DRPEGIEEEGGERDR) when compared to the reactivity against SEQ ID NO: 47 alone (n=6, most left-hand hatched bar, <0% ratio). For LTNP sera that only had a low response to SEQ ID NO: 47, this effect was enhanced when SEQ ID NOs: 47 and 6 were combined. This demonstrates that the C5:gp41 complex has the ability to capture and increase the response dramatically, even when the response from C5 alone is low; FIG. 1 shows that OD was high in the serum samples that only showed binding to SEQ ID NO: 47. However, when combined with the gp41 sequence, the responses to C5 alone were reduced since antibodies now preferably bound the combination.

FIG. 2 shows the magnitude of responses in individual sera from LTNP, chronically infected patients and blood donors to SEQ ID NO: 47 alone and SEQ ID NO: 47 in combination with SEQ ID NO: 6 (DRPEGIEEEGGERDR). There was a greater response to SEQ ID NO: 47 alone and SEQ ID NO: 47 combined with SEQ ID NO: 6 (DRPEGIEEEGGERDR). among LTNP patients compared to patients chronically infected with HIV. The median OD value for binding to SEQ ID NO: 47 and SEQ ID NO: 6 in combination is higher than binding to SEQ ID NO: 47 alone for both LTNP and patients chronically infected with HIV, showing that combination with SEQ ID NO:6 improved seroreactivity. Responses in blood donors are consistently low, there is a very tight interquartile range and no difference in seroreactivity to C5 alone or in combination with SEQ ID NO: 6 (DRPEGIEEEGGERDR) in this negative control.

A Wilcoxon rank-test performed on the OD-values derived from SEQ ID NOs: 47 and 6 combined on LTNP-sera and the OD-values derived from SEQ ID NOs: 47 and 6 combined on HIV-sera, gives that the true median differs within a 25% confidence-interval.

Example 5

Immunological Studies
Rabbit Immunizations

New Zealand White female rabbits (n=3) were immunized intradermally at weeks 0, 2 & 6 with 1 ml of BI400-B vaccine consisting of 500 µg BI400-B in 50% V/V Freund's adjuvant (i.e. Complete Freund's adjuvant used for priming, followed by boostings with Incomplete Freund's adjuvant). Individual blood serum was isolated for ELISA.

Direct ELISA for Human Sera 50-100 µl of a mixture of BI400-015 and -201 (pre-incubated in Coating buffer—0.05M Na$_2$CO$_3$ pH9.6; denoted CB—in cold at 16 µg/ml for each peptide 1-3 days prior to coating) or just CB (background control) was used for coating wells in microtiter plates at 4° C. overnight. The microtiter plates were then washed 3× with washing buffer (PBS+1% v/v Triton-X100; denoted WB), followed by 2 h blocking at room temperature (RT) with 200 µl/well of blocking buffer (PBS+1% w/v BSA). Plates were then washed 3× with WB, followed by 1 h incubation at 37° C. with 50-70 µl/well of added human (serial dilutions ranging from 1:1-1:250 in dilution buffer (PBS+1% v/v Triton-X100+1% w/v BSA; denoted DB)). Plates were then washed 6× with WB, followed by 1 h incubation at RT with 70 µl/well of Alkaline Phosphatase-conjugated Protein G (3 µg/ml in DB; Calbiochem 539305). Plates were then washed 6× with WB, followed by 10-60 min incubation at room temperature with 100 µl/well of 0.3% w/v of Phenophtalein monophosphate (Sigma P-5758). Plates were finally quenched by adding 100 µl/well of Quench solution (0.1M TRIS+0.1M EDTA+0.5M NaOH+0.01% w/v NaN$_3$; pH14), followed by ELISA reader (ASYS UVM 340) at 550 nm.

Competitive ELISA for Rabbit Sera after Immunization with BI400-B 50-100 µl of a mixture of BI400-015 and -201 (pre-incubated in Coating buffer—0.05M Na$_2$CO$_3$ pH9.6; denoted CB—in cold at 16 µg/ml for each peptide 1-3 days prior to coating) or just CB (background control) was used for coating wells in microtiter plates at 4° C. overnight. Plates were then washed 3× with washing buffer (PBS+1% v/v Triton-X100; denoted WB), followed by 2 h blocking at room temperature (RT) with 200 µl/well of blocking buffer (PBS+1% w/v BSA). Plates were then washed 3× with WB, followed by 1 h incubation at 37° C. with 60-100 µl/well of added rabbit serum samples (diluted 1:10-1:250 final concentration) preincubated together (4° C. overnight) with serial dilutions (ranging from 10-1000 µM final concentration) of 400-SEQ.B, BI400-015, BI400-201, BI400-204d, recombinant gp41 (Shin-Won Scientific, SWO 102 gp41), BI301-23 (irrelevant protein; control), no peptide (i.e. PBS; control), LTNP-sera pools (diluted 1:10 final concentration), or Blood donor sera-pools (diluted 1:10 final concentration; control). Plates were then washed 6× with WB, followed by 1 h incubation at RT with 70 µl/well of Alkaline Phosphatase-conjugated Goat-anti-Rabbit-Ig (6 µg/ml; Dako D0487). Plates were then washed 6× with WB, followed by 10-60 min incubation at RT with 100 µl/well of 0.3% w/v of Phenoftalein monophosphate (Sigma P-5758). Plates were finally quenched by adding 100 µl/well of Quench solution (0.1M TRIS+0.1M EDTA+0.5M NaOH+0.01% w/v NaN$_3$; pH14), followed by ELISA reader (ASYS UVM 340) at 550 nm.

Results

FIG. 3 demonstrates that sera from rabbits immunized with the vaccine antigen 400 SEQ-B bound to peptides corresponding to C5/gp41 (015/201) in the presence of PBS. This binding could be inhibited by recombinant gp41 as well as by peptides derived from C5 (015), gp41 (201), and C2 (204d) as well as by 400-SEQ-B itself. The binding could not be inhibited using an irrelevant peptide (B301-23).

As evident from FIG. 4, Anti-05/gp41 sera from BI400-B immunized rabbits is competitively inhibited by LTNP-sera pools, but not with BD control sera.

As shown in FIG. 5, antibodies against C5/gp41 were observed in 26/43 natural virus suppressor HIV patients with viral loads <15000 copies/ml) and in 4/15 HIV patients with viral loads above 15000 copies/ml. Furthermore, significantly (p=0.018 when using a Mann-Whitney test) higher anti-C5 IgG responses (i.e. grouped with respect to OD-value measured at same serum dilution) were observed in HIV-1 patients with viral load below 15000 copies/ml (n=43) compared to patients with viral load above 15000 copies/ml (n=15).

To conclude, the results from the immunization studies with BI400-B demonstrate that it is possible to generate peptides that elicit antibody responses to C5 and gp41/C2 not only as individual components but also as complexes. The specificity of these antibody responses is confirmed in blocking studies using specific peptide antigens (FIG. 3). Furthermore, antibodies generated to these peptides in animal models are comparable with antibodies elicited in natural HIV infection and associated with longterm nonprogression (FIG. 4). These results show that these peptides are suitable for diagnostics as well as the development of a vaccine targeting HIV-induced immune activation. The finding that BI400-B elicits antibodies that bind to the complex between gp41 and C5, and that these antibodies compete with antisera against the same complex epitopes in LTNP HIV patients indicates that it is possible to stimulate immune responses against these epitopes and thereby induce an LTNP-like condition in patients which do not themselves raise antibodies of this type against HIV.

The invention claimed is:

1. A composition comprising a first peptide, which consists of the amino acid sequence SEQ ID NO: 38, and at least one second peptide, which comprises an amino acid sequence having the formula:

$$Z^1\text{-}Z^2\text{-}Z^3\text{-}Z^4\text{-}Z^5\text{-}Z^6\text{-}Z^7\text{-}Z^8\text{-}Z^9\text{-}Z^{10}\text{-}Z^{11}\text{-}Z^{12}\text{-}Z^{13}\text{-}Z^{14}\text{-}Z^{15}\text{-}Z^{16}\text{-}Z^{17} \quad (III)$$

wherein $Z^1$ is Asp, $Z^2$ is Arg, $Z^3$ is Pro, $Z^4$ is Glu or Gly, $Z^5$ is Gly or Arg, $Z^6$ is Ile, $Z^7$ is Glu, $Z^8$ is Glu, $Z^9$ is Glu, $Z^{10}$ is Gly, $Z^{11}$ is Gly, $Z^{12}$ is Glu or is absent, $Z^{13}$ is Arg or Gln, $Z^{14}$ is Asp or Gly, $Z^{15}$ is Arg or Lys, $Z^{16}$ is Asp or Gly and $Z^{17}$ is Arg, or which comprises a subsequence of formula (III) of at least 5 amino acid residues, wherein said peptide combination is capable of inducing an antibody which can bind and stabilise the association of the C5 domain of HIV gp120 with the transmembrane domain of gp41, and wherein said first peptide and said at least one second peptide lack amino acids N-terminal of C5 in gp120.

2. The composition according to claim 1, wherein the total number of amino acid residues is 53.

3. The composition according to claim 1, wherein the first peptide and the at least one second peptide are linked via a Cys-Lys linker.

4. The composition according to claim 1, wherein the at least one second peptide comprises a subsequence of formula (III) of at least 13 amino acid residues.

5. The composition according to claim 1, wherein the at least one second peptide comprises any one of SEQ ID NOs: 39, 40, 42, and 43 with 1, 2, or 3 insertions, substitutions or deletions.

6. A composition comprising a first peptide, which consists of the amino acid sequence SEQ ID NO: 38, and at least one second peptide, which comprises 13 consecutive amino acid resides from an amino acid sequence having the formula:

$$Z^1\text{-}Z^2\text{-}Z^3\text{-}Z^4\text{-}Z^5\text{-}Z^6\text{-}Z^7\text{-}Z^8\text{-}Z^9\text{-}Z^{10}\text{-}Z^{11}\text{-}Z^{12}\text{-}Z^{13}\text{-}Z^{14}\text{-}Z^{15}\text{-}Z^{16}\text{-}Z^{17} \quad (III)$$

wherein $Z^1$ is Asp, $Z^2$ is Arg, $Z^3$ is Pro, $Z^4$ is Glu or Gly, $Z^5$ is Gly or Arg, $Z^6$ is Ile, $Z^7$ is Glu, $Z^8$ is Glu, $Z^9$ is Glu, $Z^{10}$ is Gly, $Z^{11}$ is Gly, $Z^{12}$ is Glu or is absent, $Z^{13}$ is Arg or Gln, $Z^{14}$ is Asp or Gly, $Z^{15}$ is Arg or Lys, $Z^{16}$ is Asp or Gly and $Z^{17}$ is Arg, wherein said peptide combination is capable of inducing an antibody which can bind and stabilise the association of the C5 domain of HIV gp120 with the transmembrane domain of gp41, and wherein said peptide combination lacks amino acids N-terminal of C5 in gp120, and the at least one first and at least one second peptides together consist of 53 amino acid residues, and the first peptide and the second peptide are linked via a Cys-Lys linker.

7. The composition according to claim 1 further comprising a pharmaceutically acceptable diluent or vehicle and optionally an immunological adjuvant.

8. The composition according to claim 6 further comprising a pharmaceutically acceptable diluent or vehicle and optionally an immunological adjuvant.

9. A composition comprising a first peptide, which has the amino acid sequence of formula IV:

$$S^1\text{-}X^9\text{-}S^2 \quad (IV)$$

wherein $S^1$ is the amino acid sequence GAKRRVVG-GCGGAKRRVVQREKRAG (SEQ ID NO: 60), $X^9$ is selected from Gln, Glu, Asn and Asp, $S^2$ is the amino acid sequence REKRA (SEQ ID NO: 61) and, at least one second peptide, which comprises an amino acid sequence having the formula V:

$$Z^1\text{-}Z^2\text{-}Z^3\text{-}Z^4\text{-}Z^5\text{-}Z^6\text{-}Z^7\text{-}Z^8\text{-}Z^9\text{-}Z^{10}\text{-}Z^{11}\text{-}Z^{12}\text{-}Z^{13}\text{-}Z^{14}\text{-}Z^{15}\text{-}Z^{16}\text{-}Z^{17}Z^{18}\text{-}Z^{19}\text{-}Z^{20}\text{-}Z^{21}\text{-}Z^{22}\text{-}Z^{23}\text{-}Z^{24} \quad (V)$$

wherein $Z^1$ is Gly, $Z^2$ is Lys, $Z^3$ is Gly, $Z^4$ is Gly, $Z^5$ is Ile, $Z^6$ is Glu, $Z^7$ is Glu, $Z^8$ is Glu, $Z^9$ is Gly, $Z^{10}$ is Gly, $Z^{11}$ is Glu or is absent, $Z^{12}$ is Arg or Gln, $Z^{13}$ is Asp, $Z^{14}$ is Arg, $Z^{15}$ is Asp, $Z^{16}$ is Arg, $Z^{17}$ is Gly, $Z^{18}$ is Gly, $Z^{19}$ is Glu or is absent, $Z^{20}$ is Arg or Gln, $Z^{21}$ is Asp, $Z^{22}$ is Arg, $Z^{23}$ is Asp, $Z^{24}$ is Arg, or which comprises a subsequence of formula (V) of at least 5 amino acid residues, wherein the first peptide and at least one second peptide are linked via a Cys-Lys linker, by an amide bond between the (2-oxo-ethyl) derivatized $Cys^{10}$ of the first peptide and $Lys^2$ of the at least second peptide, said peptide combination is capable of inducing an antibody which can bind and stabilise the association of the C5 domain of HIV gp120 with the transmembrane domain of gp41, and wherein said first peptide and at least one second peptide lack amino acids N-terminal of C5 in gp120.

10. The composition according to claim 9, wherein $X^9$ is selected from Gln and Glu.

11. A composition according to claim 10 further comprising a pharmaceutically acceptable diluent or vehicle and optionally an immunological adjuvant.

* * * * *